(12) United States Patent
Van Gompel et al.

(10) Patent No.: US 6,361,527 B1
(45) Date of Patent: Mar. 26, 2002

(54) THREE-DIMENSIONAL POCKET GARMENT

(75) Inventors: Paul Theodore Van Gompel, Hortonville; Yung Hsiang Huang, Appleton, both of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/422,319

(22) Filed: Oct. 21, 1999

(51) Int. Cl.$^7$ .................................................. A61F 13/15
(52) U.S. Cl. ............................. 604/385.25; 604/385.3; 604/385.29
(58) Field of Search ..................... 604/358, 385.01, 604/385.16, 385.21, 385.22, 385.23, 385.24, 385.26, 385.29, 386, 387, 389, 391, 394, 396, 385.3

(56) References Cited

U.S. PATENT DOCUMENTS

| | | |
|---|---|---|
| 3,807,402 A | 4/1974 | Miller et al. |
| 3,848,595 A | 11/1974 | Endres |
| 3,901,236 A | 8/1975 | Assarsson et al. |
| 4,076,663 A | 2/1978 | Masuda et al. |
| 4,108,179 A | 8/1978 | Schaar |
| 4,286,082 A | 8/1981 | Tsubakimoto et al. |
| 4,663,220 A | 5/1987 | Wisneski et al. |
| 4,699,823 A | 10/1987 | Kellenberger et al. |
| 4,704,116 A | 11/1987 | Enloe |
| 4,916,005 A | 4/1990 | Lippert et al. |
| 4,938,753 A | 7/1990 | Van Gompel et al. |
| 5,019,073 A | 5/1991 | Roessler et al. |
| 5,226,992 A | 7/1993 | Morman |
| 5,399,219 A | 3/1995 | Roessler et al. |
| 5,486,166 A | 1/1996 | Bishop et al. |
| 5,490,846 A | 2/1996 | Ellis et al. |
| 5,540,796 A | 7/1996 | Fries |
| 5,562,650 A | 10/1996 | Everett et al. |
| 5,595,618 A | 1/1997 | Fries et al. |
| 5,605,735 A | 2/1997 | Zehner et al. |
| 5,624,429 A | 4/1997 | Long et al. |
| 5,746,730 A | * 5/1998 | Suzuki et al. ............ 604/385.2 |
| 5,810,800 A | * 9/1998 | Hunter et al. ............ 604/385.2 |
| 6,132,410 A | * 10/2000 | Van Gompel et al. ... 604/385.1 |

FOREIGN PATENT DOCUMENTS

| | | |
|---|---|---|
| EP | 0 217 032 A2 | 4/1987 |
| WO | WO 95/16425 A2 | 6/1995 |
| WO | WO 96/32084 A1 | 10/1996 |

OTHER PUBLICATIONS

American Society for Testing Materials (ASTM) Designation: D 882–95a, "Standard Test Method for Tensile Properties of Thin Plastic Sheeting," pp. 182–187, published Dec. 1995.
Federal Test Method Standard (FTMS) No. 191A, Method 5514, "Water Resistance of Cloth; Low Range, Hydrostatic Pressure Method," Jul. 20, 1978, 3 pages.
TAPPI Official Test Method T 543 om–94, "Bending Resistance of Paper (Gurley Type Tester)," published by the TAPPI Press, Atlanta, Georgia, pp. 1–7.

* cited by examiner

Primary Examiner—John G. Weiss
Assistant Examiner—Jamisue Webb
(74) Attorney, Agent, or Firm—Paul Yee

(57) ABSTRACT

An integral absorbent article (10) has a longitudinal length direction (27), a lateral width direction (25), and at least one edge margin (20, 22). The article includes a substantially liquid-impermeable backsheet layer (30), a liquid permeable topsheet layer (28), and a retention portion (48) sandwiched between the backsheet and topsheet layers. The edge margin (20, 22) can include an elastomeric member (34) joined to provide elastomerically contracted gathers (66) in the edge margin. The edge margin (20, 22) can also include a restraint (84) applied to an appointed portion of its corresponding gathers (66) to operatively restrict a re-expansion of a constrained section (94) of the corresponding gathers (66).

35 Claims, 12 Drawing Sheets

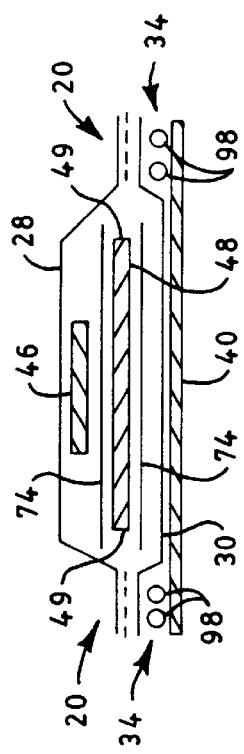
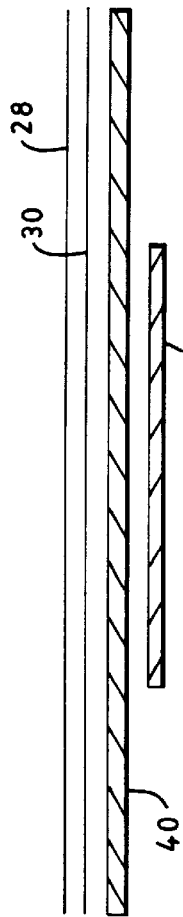
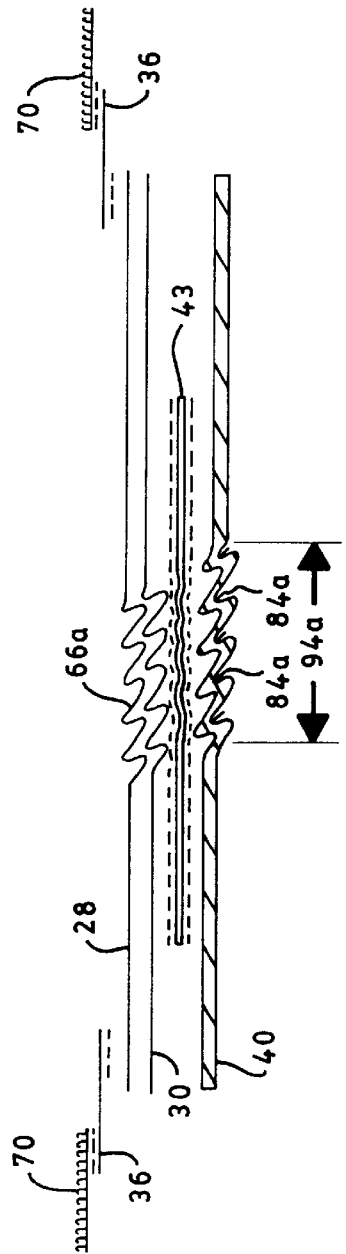

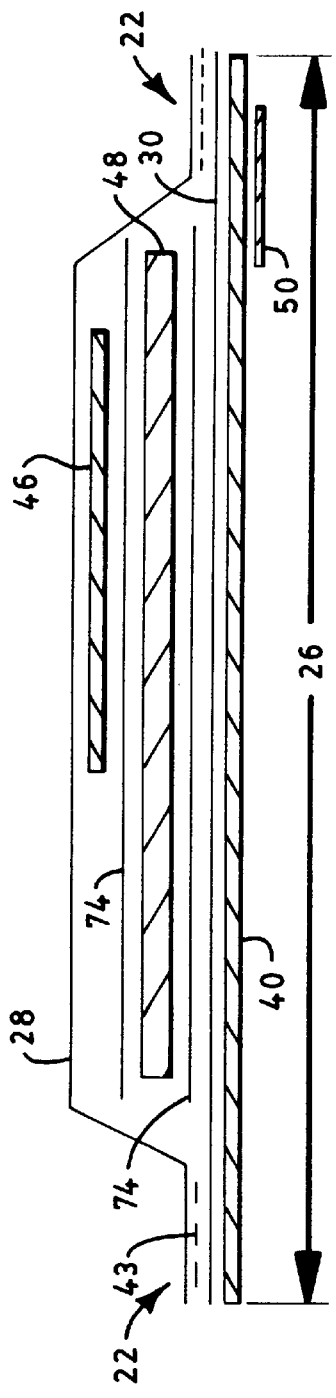
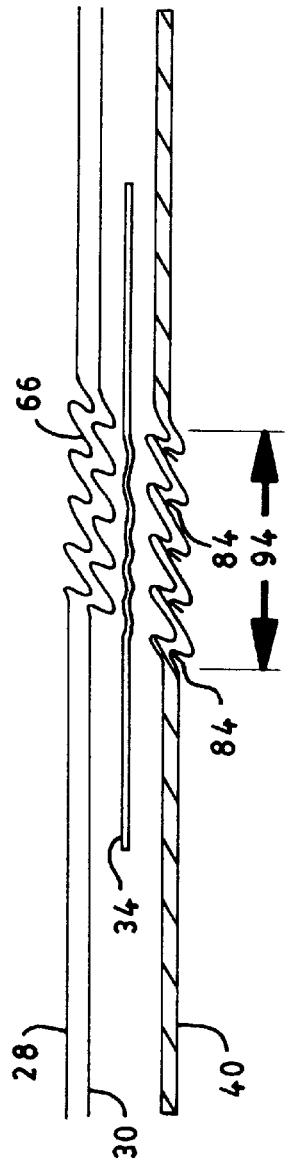
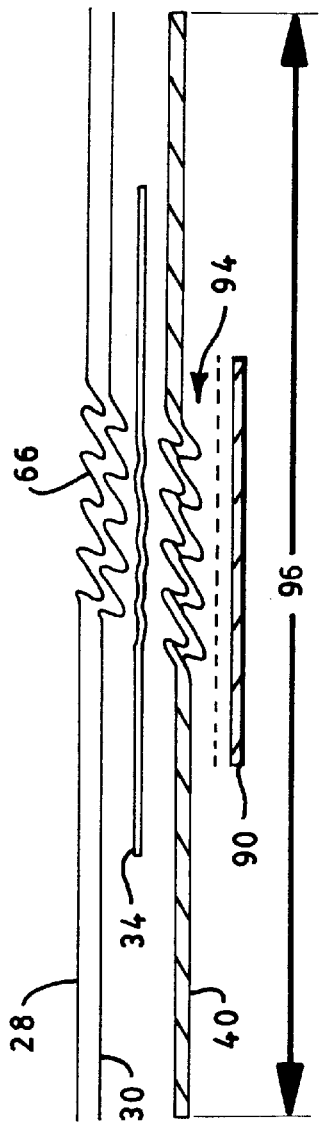
FIG. 1E
FIG. 1F
FIG. 1G

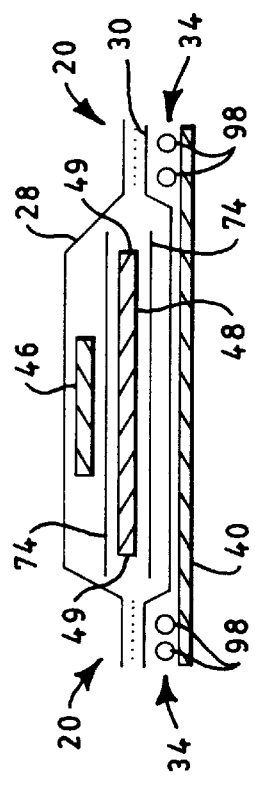
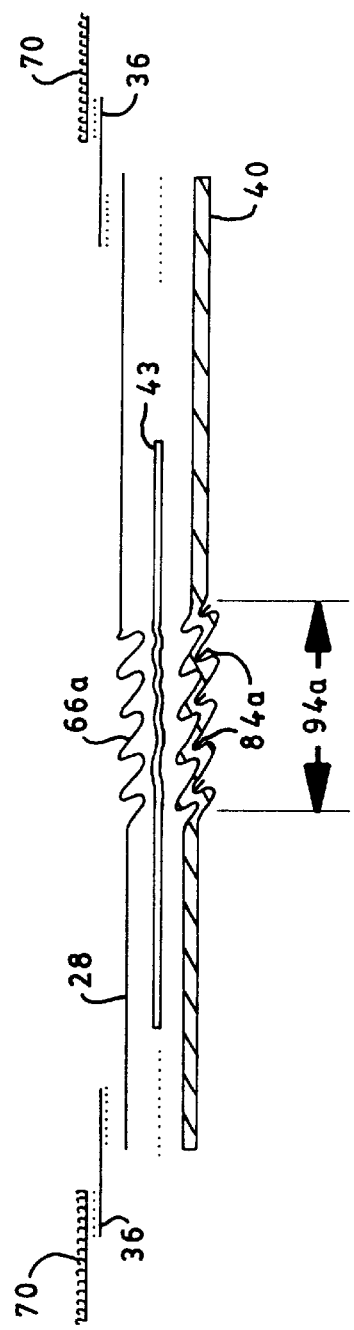
FIG. 2A
FIG. 2B
FIG. 2C

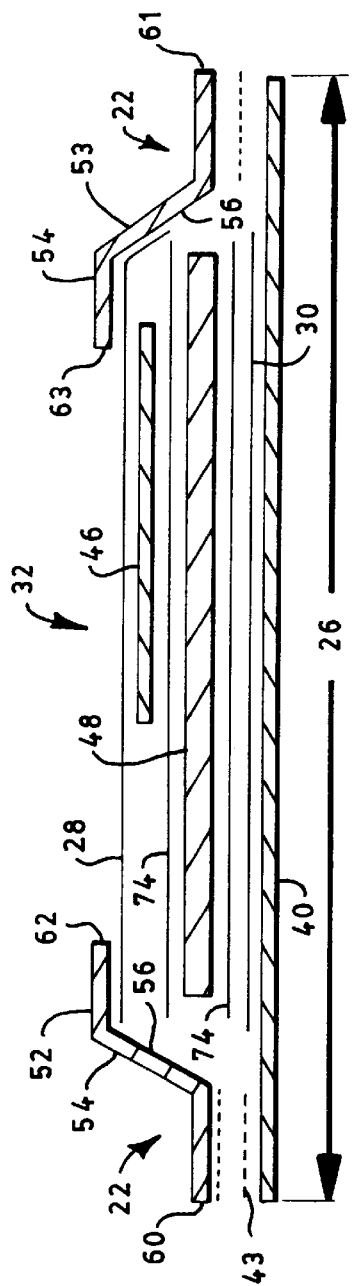
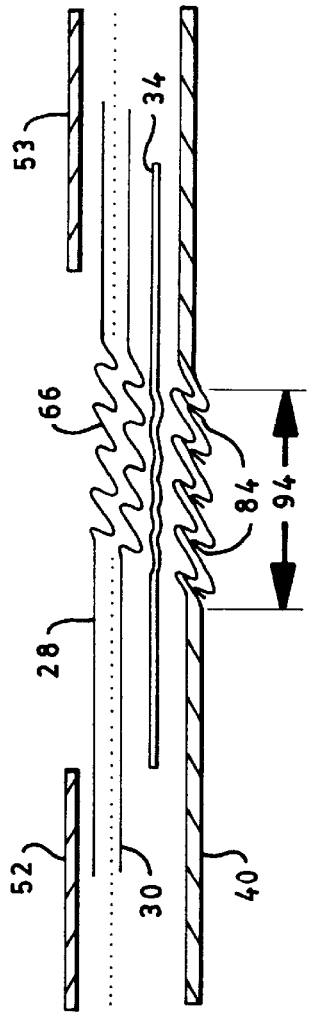
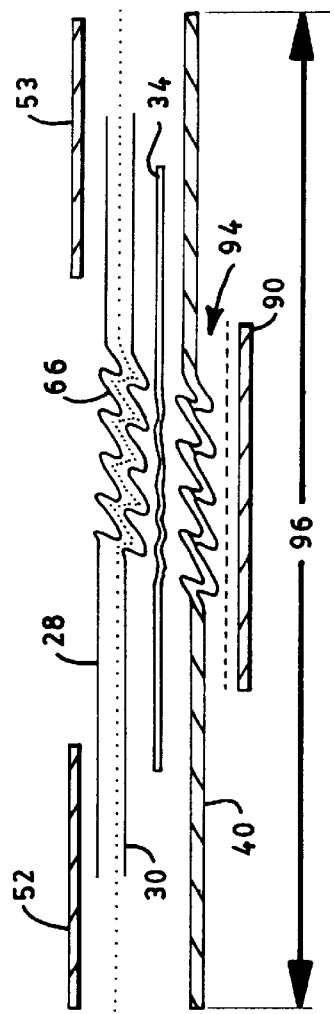
FIG. 3D
FIG. 3E
FIG. 3F

THREE-DIMENSIONAL POCKET GARMENT

FIELD OF THE INVENTION

The present invention relates to personal care articles. More particularly, the present invention relates to absorbent articles, desirably disposable absorbent articles, which have a distinctive system of leg elastics.

BACKGROUND OF THE INVENTION

Conventional absorbent articles, such as disposable diapers and other disposable garment articles, have typically employed adhesive or mechanical fasteners which attach appointed waistband sections of the articles around a wearer. Various configurations of waist elastics and leg elastics to produce elasticized gathers along the waistbands and leg openings of conventional articles. In addition, elasticized liners, and elasticized outercovers have been employed on garment articles to help provide and maintain the fit of the articles about the body contours of the wearer.

Other conventional absorbent garments have included folded pleats in the outercover. The pleats are arranged to expand open as the garment absorbs liquids.

The external surfaces of such disposable absorbent products may include a nonwoven fibrous material or a matte-finished film material. In some arrangements, pattern embossments have been formed into outer surface of the outercover to provide a decorative pattern.

Still other disposable garments have incorporated an absorbent composite jointed to an outercover composed of elastomeric materials, such as elastomeric, stretch-bonded-laminate materials. Such materials have included a layer meltblown elastomeric fibers which has been stretched and sandwiched between facing layers composed of a polypropylene spunbond nonwoven fabric. The meltblown layer has typically been pattern-bonded to the facing layers with thermal bonds, sonic bonds and/or adhesive bonds.

Conventional garment articles, such as those described above, however, have not provided desired levels of high absorbency, resistance to leakage, low cost and ease of manufacture. The conventional articles have also not provided desired levels of close fit, particularly around the legs of a wearer. Additionally, the conventional articles have not been sufficiently able to form and maintain of desired void spaces in the article during use. As a result, there has been a continued need for garments having improvements in such properties.

BRIEF DESCRIPTION OF THE INVENTION

Generally stated, the present invention provides an absorbent article having a longitudinal length direction, a lateral width direction, and at least one edge margin. The article includes a substantially liquid-impermeable backsheet layer, a liquid permeable topsheet layer, and a retention portion sandwiched between the backsheet and topsheet layers. The edge margin can include an elastomeric member joined to provide elastomerically contracted gathers in the edge margin. The edge margin can also include a restraint applied to an appointed portion of its corresponding gathers to operatively restrict a re-expansion of a constrained section of the corresponding gathers.

In its various aspects, the article of present invention can provide an article having improved fit, improved absorbency and improved resistance to leakage. The article may also be produced at lower cost and with greater efficiency. In particular, the constrained sections of the elasticized gathers can advantageously provide an article having a distinctive three-dimensional absorbent pocket. The size and location of the pocket or space can be determined by the size and the location of a constrained portion of the elastic gathers in each side margin. Additionally, the various configurations of the invention can provide a closer fit, particularly around the legs of a wearer, and the improved fit can help reduce leakage.

BRIEF DESCRIPTION OF THE DRAWINGS

The present invention will be more fully understood and further advantages will become apparent when reference is made to the following detailed description of the invention and the drawings, in which:

FIG. 1B representatively shows a schematic, expanded, lateral cross-sectional view taken with respect to the line 1B—1B of FIG. 1;

FIG. 1C representatively shows a schematic, expanded, lateral cross-sectional view taken with respect to the line 1C—1C of FIG. 1;

FIG. 1D representatively shows a schematic, expanded, lateral cross-sectional view taken with respect to the line 1D—1D of FIG. 1;

FIG. 1E representatively shows a schematic, expanded, longitudinal cross-sectional view taken with respect to the line 1E—1E of FIG. 1;

FIG. 1F representatively shows a schematic, expanded, longitudinal cross-sectional view of constrained leg gathers taken with respect to the line 1F—1F of FIG. 1;

FIG. 1G representatively shows a schematic, expanded, longitudinal cross-sectional view of an alternative configuration of the constrained gathers taken with respect to the section of the article representatively shown in FIG. 1F;

FIG. 2A representatively shows a schematic, expanded, lateral cross-sectional view taken with respect to the line 2A—2A of FIG. 2;

FIG. 2B representatively shows a schematic, expanded, lateral cross-sectional view taken with respect to the line 2B—2B of FIG. 2;

FIG. 2C representatively shows a schematic, expanded, lateral cross-sectional view taken with respect to the line 2C—2C of FIG. 2;

FIG. 3D representatively shows a schematic, expanded, longitudinal cross-sectional view taken with respect to the line 3D—3D of FIG. 3;

FIG. 3E representatively shows a schematic, expanded, longitudinal cross-sectional view of constrained leg gathers taken with respect to the line 3E—3E of FIG. 3;

FIG. 3F representatively shows a schematic, expanded, longitudinal cross-sectional view of an alternative configuration of the constrained gathers taken with respect to the section of the article representatively shown in FIG. 3E;

DETAILED DESCRIPTION OF THE INVENTION

The various aspects and embodiments of the invention will be described in the context of a disposable absorbent article, such as a disposable diaper. It is, however, readily apparent that the present invention could also be employed with other articles, such as feminine care articles, children's training pants, incontinence garments and the like. Typically, the disposable articles are intended for limited use and are not intended to be laundered or otherwise cleaned for reuse. A disposable diaper, for example, is discarded after it has become soiled by the wearer. Optionally, a disposable diaper may include a single-use, absorbent insert, and a limited-use outer cover which may be reused several times.

It should also be noted that, when employed in the present disclosure, the terms "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof.

Figure 1:
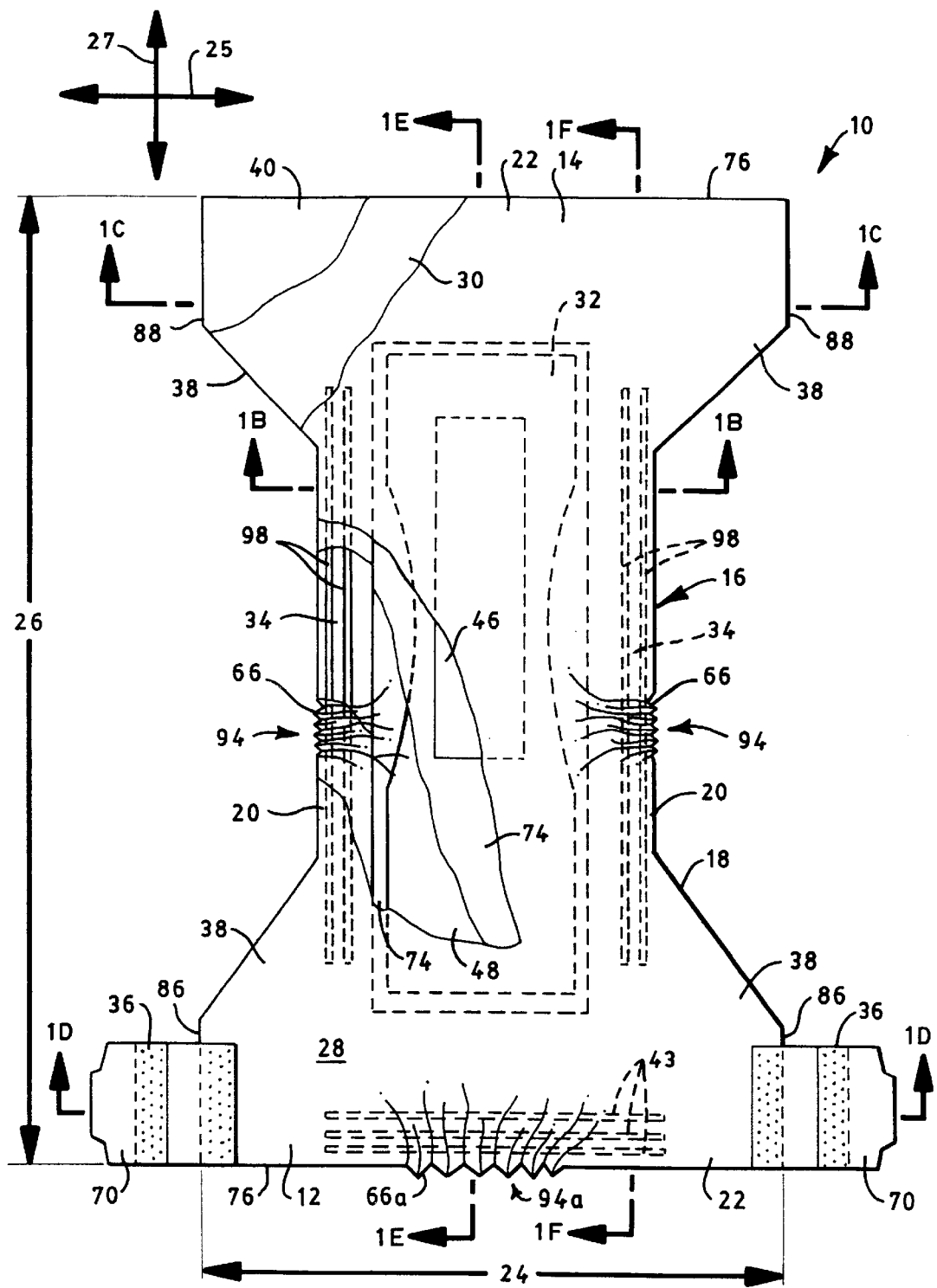
FIG. 1 representatively shows a partially cut-away, top plan view of the inward, bodyside surface of an article of the invention.

With reference to FIGS. 1 through 1G, an article, such as the illustrated absorbent article provided by the representatively shown, integral diaper 10, can have a longitudinal length direction 27, a lateral cross-directional width direction 25, and at least one edge margin provided at an appointed region along a marginal or terminal edge of the article. Additionally, the article can include a substantially liquid-impermeable backsheet layer 30, a liquid permeable topsheet layer 28, and a retention portion 48 which is sandwiched between the backsheet and topsheet layers. The edge margin can include an elastomeric member joined to provide a set of elastomerically contracted gathers 66 in the edge margin. The side margin can also include a restraint 84 applied to an appointed portion of its corresponding set of gathers, and each restraint can be configured to operatively restrict a re-expansion of a constrained section of its corresponding set of gathers. The restraint can thereby provide a shortened, constrained length 96 along its corresponding side margin, and the constrained length is relatively shorter than the article length 26.

The selected edge margin may be a lateral side margin 20 and/or a longitudinal end margin 22. For example, the article can include a pair of laterally opposed side margins 20, and can have first and second, longitudinally opposed end margins 22. In desired arrangements, each side margin 20 can include an elastomeric member 34 joined to provide a corresponding set of elastomerically contracted gathers 66 in its associated side margin. Each side margin 20 can also include a restraint 84 applied to an appointed portion of its corresponding set of side gathers 66, and each restraint can be configured to operatively restrict a re-expansion of a constrained section 94 of its corresponding set of gathers 66. In other configurations, either or both end margins 22 can include an elastomeric member joined to provide a corresponding set of elastomerically contracted end gathers 66a in its associated end margin. Either or both end margins 22 can also include a restraint 84a applied to an appointed portion of its corresponding set of gathers 66a, and each restraint can be configured to operatively restrict a re-expansion of a constrained section 94a of its corresponding set of gathers 66a.

Figure 2:
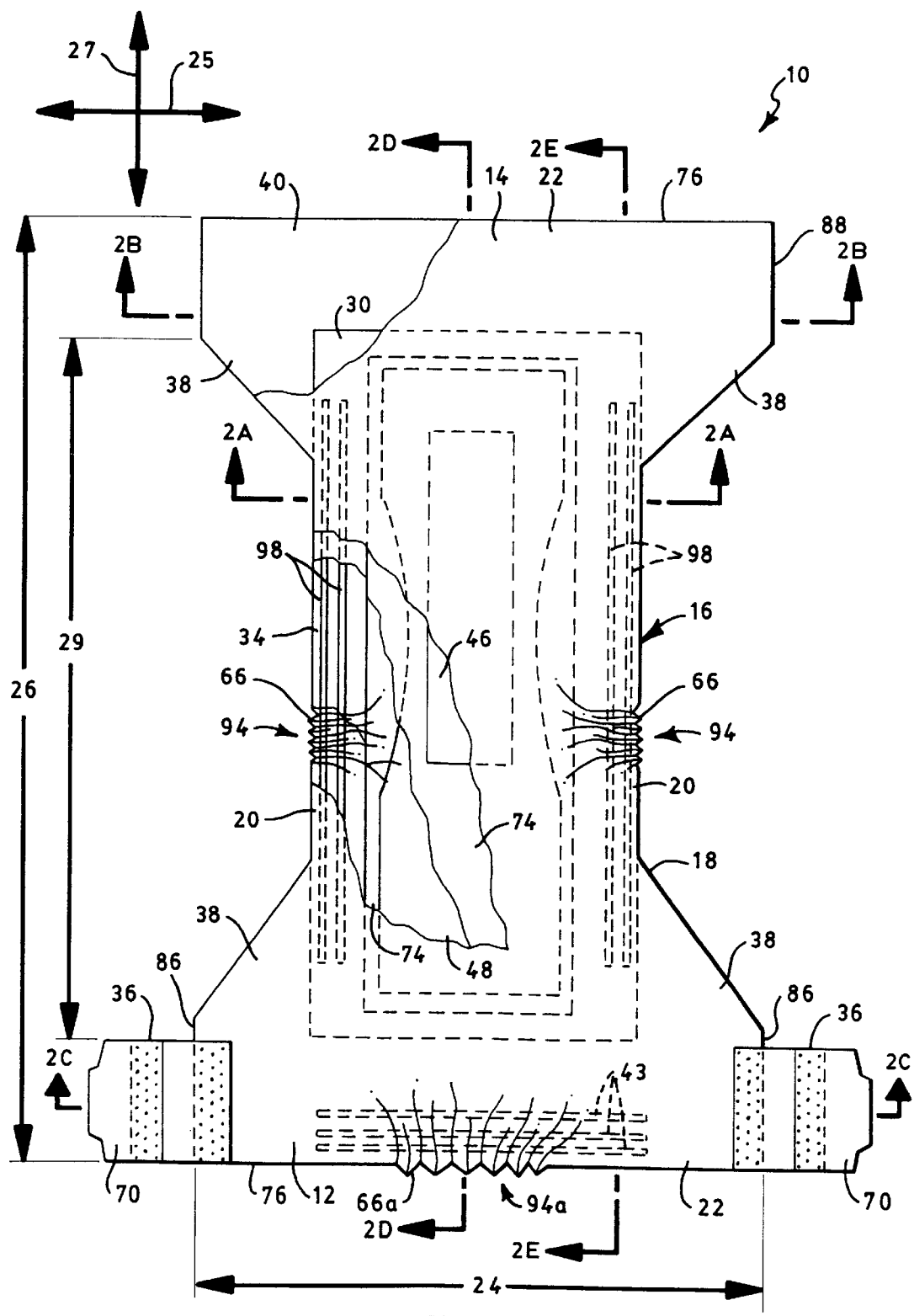
FIG. 2 representatively shows a partially cut-away, top plan view of the inward surface of another example of an article of the invention in which a length of a substantially liquid-impermeable member or layer has been reduced.
Figure 2D:
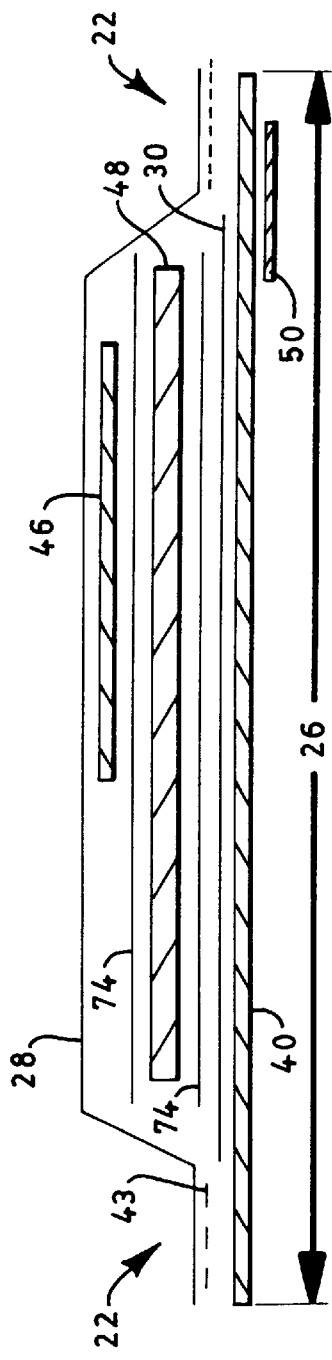
FIG. 2D representatively shows a schematic, expanded, longitudinal cross-sectional view taken with respect to the line 2D—2D of FIG. 2.
Figure 2E:
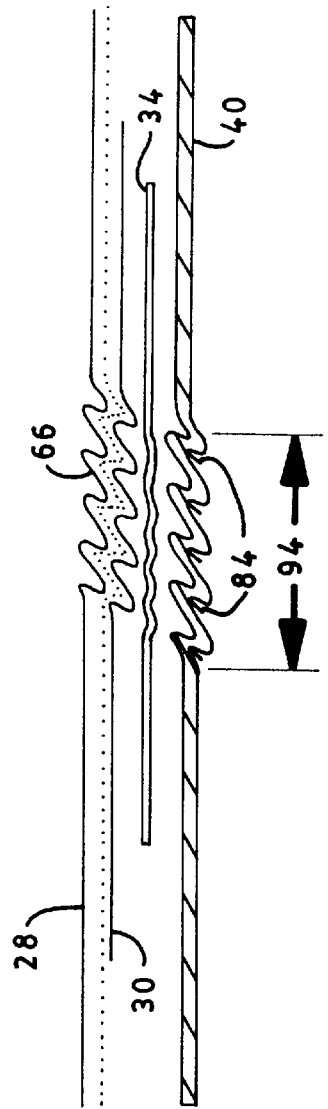
FIG. 2E representatively shows a schematic, expanded, longitudinal cross-sectional view of constrained leg gathers taken with respect to the line 2E—2E of FIG. 2.
Figure 2F:
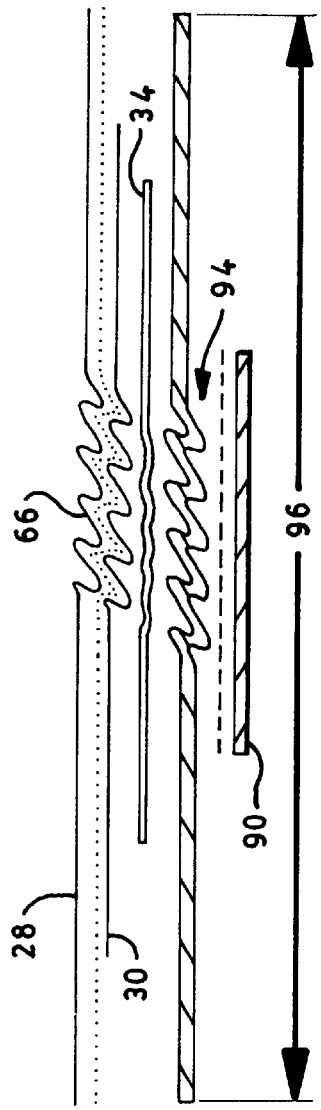
FIG. 2F representatively shows a schematic, expanded, longitudinal cross-sectional view of an alternative configuration of the constrained gathers taken with respect to the section of the article representatively shown in FIG. 2E.

With reference to FIGS. 2 through 2F, particular aspects of the article can include a component which has a longitudinal, component length 29 which is shorter than the article length 26. In the representatively shown configuration, the shorter component is the backsheet layer, and the outercover layer 40 extends longitudinally beyond the terminal end edges of the backsheet layer 30. Additionally, the outercover layer can extend laterally beyond the lateral side edges of the backsheet layer. In desired arrangements, the outercover layer can extend laterally beyond the lateral side edges of the backsheet layer in at least one waistband portion 12 and/or 14 of the article.

Figure 3:
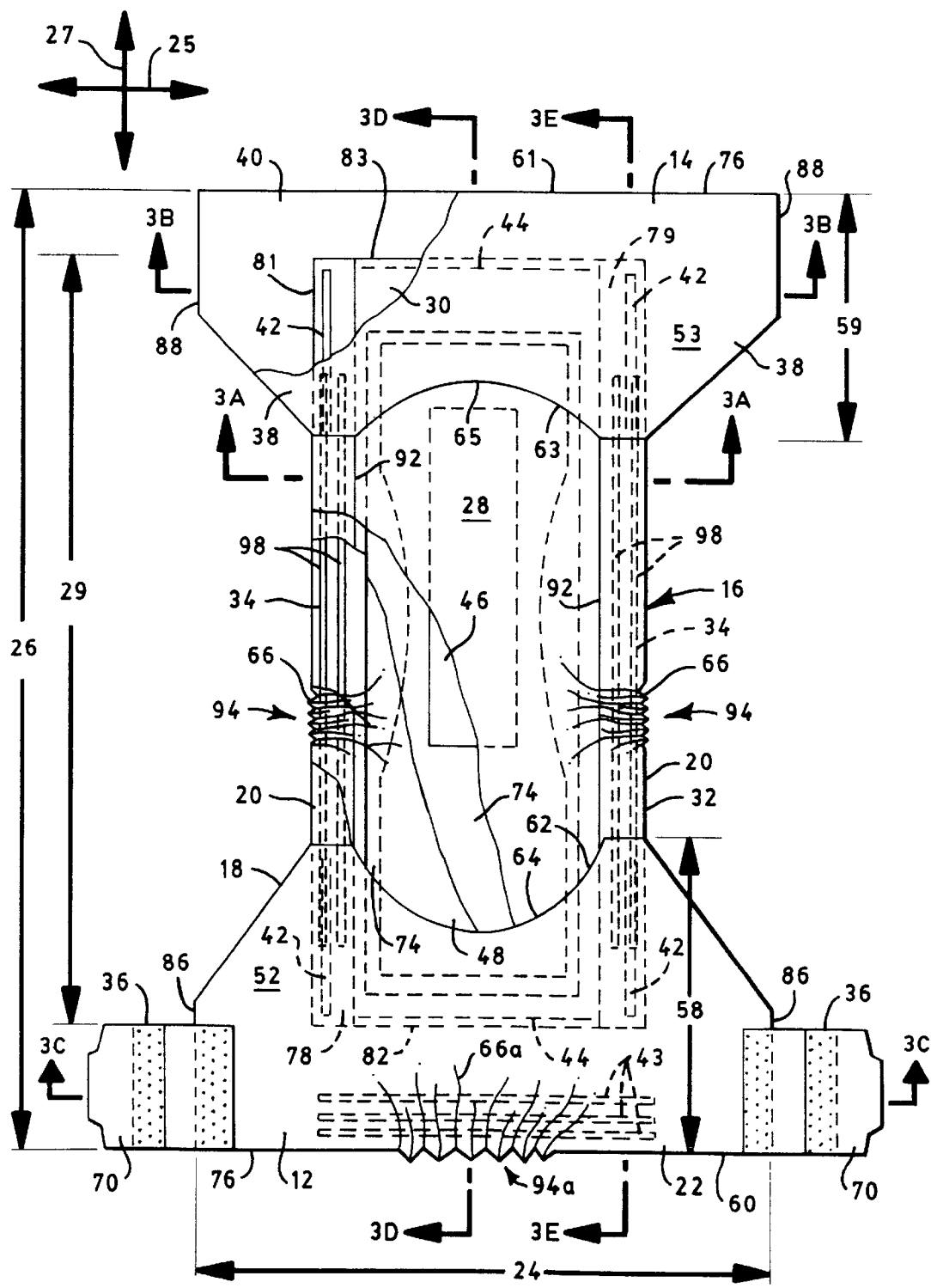
FIG. 3 representatively shows a partially cut-away, top plan view of the inward surface of an article of the invention having an absorbent composite attached to front and back body panels.

With reference to FIGS. 3 through 3F, other aspects of the article can include an absorbent composite 32 having first and second longitudinally opposed end regions 78 and 79, respectively, a pair of laterally opposed side margins 20, an inward bodyside surface, an outward surface, and longitudinally terminal end edges 82. The absorbent composite can include the substantially liquid-impermeable backsheet layer 30, the liquid permeable topsheet layer 28, and the retention portion 48 sandwiched between the backsheet and topsheet layers. Each side margin 20 of the absorbent composite 32 can include an elastomeric member 34 joined to provide a corresponding set of elastomerically contracted gathers 66 in each side margin. Each side margin 20 of the absorbent composite 32 can also include a restraint 84 applied to an appointed portion of the gathers 66 in that side margin. Each restraint can operatively restrict a re-expansion of a corresponding constrained section 94 of the gathers 66 in each side margin.

In other aspects, the retention portion 48 can have laterally opposed, terminal side edges 49, and the absorbent composite 32 can include a pair of laterally opposed side margins 20 which extend laterally beyond the side edges 49 of the retention portion 48. A first body panel 52 may also be joined to the first longitudinal end 78 of the absorbent composite 32. The first body panel 52 has a body side surface 54, an outward surface 56, an outboard terminal end edge 60, and a relatively inboard terminal end edge 62. Additionally, each side margin 20 of the absorbent composite 32 can be secured to the outward surface 56 of the first body panel 52. Such securement can, for example, include at least one body panel attachment 42. Desirably, the securement can include a predetermined system or array of body panel attachments.

In additional aspects, a second body panel 53 may be joined to a longitudinally opposed, second end region 79 of the absorbent composite 32. In desired configurations, each side margin 20 of the absorbent composite 32 can be secured to the outward surface 56 of the second body panel 53. Similar to the configuration provided with the first body panel, such securement can, for example, include at least one body panel attachment 42, and desirably, the securement can include a predetermined system of body panel attachments. The first body panel 52 may, for example, be joined to provide the back waistband portion 12 of the article, and the second body panel 53 may be joined to a longitudinally opposed end of the absorbent composite 32 to provide the front waistband portion 14 of the article.

In further aspects of the invention, an expandable attachment section 92 may be employed at each of the side margins 20 to connect the absorbent composite 32 to its associated body panels 52 and/or 53. Additionally, each body panel attachment 42 may be located proximate a longitudinally extending, terminal side edge of its corresponding side margin 20. Such placement can help facilitate and accommodate the expansion of the absorbent composite as it absorbs liquid. Accordingly, a corresponding, expandable attachment section 92 can be provided along at least a portion of each associated side region 20 of the article. Each expandable attachment section 92 can be expandable at least outwardly or at least along the lateral cross-direction of the article width 24, and each expandable attachment section can be configured to secure its correspondingly joined side edge region of the absorbent composite to the outward surface 56 of the first body panel 52.

Figure 3A:
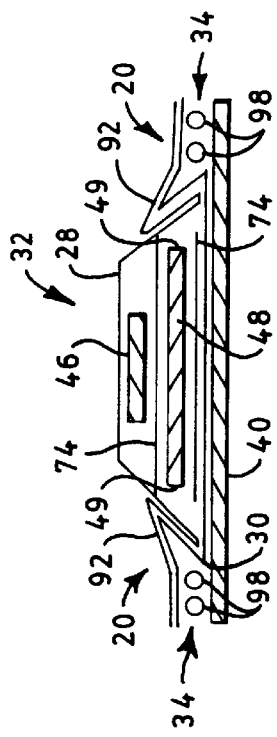
FIG. 3A representatively shows a schematic, expanded, lateral cross-sectional view taken with respect to the line 3A—3A of FIG. 3.
Figure 3B:
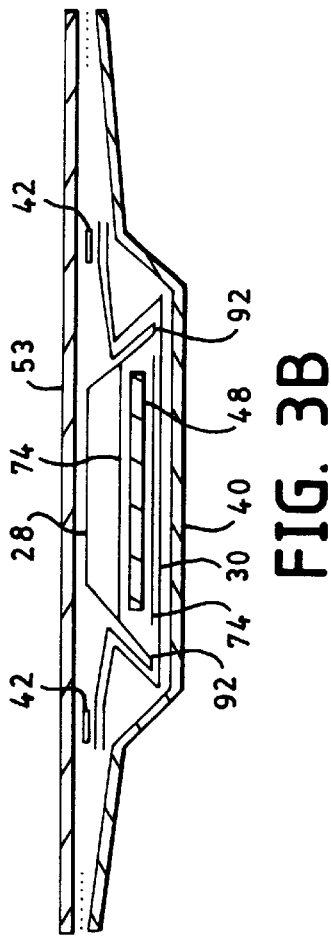
FIG. 3B representatively shows a schematic, expanded, lateral cross-sectional view taken with respect to the line 3B—3B of FIG. 3.
Figure 3C:
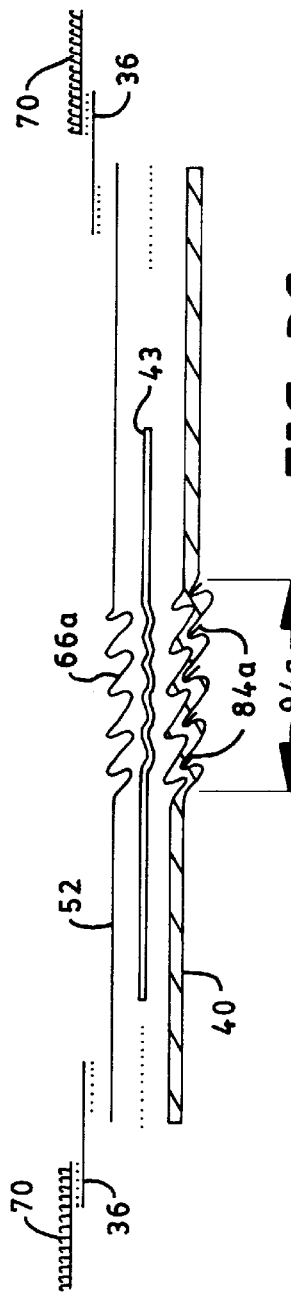
FIG. 3C representatively shows a schematic, expanded, lateral cross-sectional view taken with respect to the line 3C—3C of FIG. 3.

With reference to FIGS. 3 through 3B, at least one of the topsheet and backsheet layers 28 and 30, respectively, can extend laterally beyond the side edges 49 of the retention portion 48 to provide the laterally opposed side margins 20 of the absorbent composite 32. In an alternative configuration, each side margin 20 may include a separately provided member which is operatively assembled to the absorbent composite to provide the desired side margins 20.

The various aspects of the invention, taken alone or in combination, can advantageously provide an article having a distinctive three-dimensional absorbent pocket. The article of the invention can, for example, incorporate longitudinal side regions operatively held in a relatively shortened configuration. Accordingly, a longitudinal length of a medial portion of the article can be relatively longer than the shortened side regions of the article. In particular aspects, a post-bonding or other post-restraining of the gathered side regions can be employed to operatively constrain and shorten the longitudinally extending side regions of the article. The laterally inboard, longitudinally extending, medial section of the article, and particularly the laterally inboard, medial section of the absorbent structure, can operatively maintain their original length. The resulting differences in length can thereby create a three-dimensional pocket or space within the article, and can particularly create a three-dimensional pocket or space within the absorbent structure. The size and location of the pocket or space can be determined by various factors, such as the size, shape, extent, distribution, pattern arrangement, location, and the like, of the constrained portion of the elasticized gathers in each side margin.

In conventional disposable articles, such as diapers, the longitudinally extending side regions of the article have typically been elastically gathered. For example, each of the longitudinal side regions of the article can include an elongated, stretched elastomeric member which is attached to the side margin. When the stretching force is released, the elastomeric member can contract and gather its attached side region. When the article is applied to the wearer, however, the side regions of the article are typically stretched and elongated to approximately equal the length of the inboard, medial region of the article. As a result, any space or volume that was created by the article gathering typically becomes stretched out and lost.

In the configurations provided by the present invention, however, the constrained sections of the gathers in combination with the relatively unconstrained inboard length of the medial section of the article can more effectively create and maintain an operative containment space or volume within the absorbent structure, and the retained volume can provide an improved mechanism and configuration for holding body wastes. In addition, the perimeter of the article along the leg openings can be more effectively held in a shortened configuration, and the firmly held shortened length of the side margins can help create a more closely fitting and more leakage resistant gasket around the legs of the wearer.

Where the article of the invention incorporates an absorbent composite and expandable attachment sections which join the absorbent composite to the body panels, the expandable attachment sections can allow the absorbent composite to increase in volume during use while allowing the body panel to maintain a close and conforming fit around the waist and torso of the wearer's body. The body panel can also better provide a more effective barrier between the wet absorbent composite and the wearer's skin. Where leg elastics and appointed portions of the expandable attachment sections are provided at the lateral side margins of the absorbent composite in the intermediate, crotch portion of the diaper, those elasticized and expandable side margins can allow the absorbent composite to grow in volume outwardly, away from the wearer, substantially without affecting the positioning and close fit of the leg elastics about the wearer's legs. As a result, the article of the invention can advantageously provide improved absorbency with reduced leakage.

With reference again to FIGS. 1 through 1G, the article can have a first waistband portion 12 positioned at the back or rear of the diaper, and a second or front waistband portion 14 positioned longitudinally opposite of the first waistband portion 12. An intermediate, crotch portion 16 interconnects the first and second waistband portion 12 and 14, respectively. In the shown configurations, the intermediate portion is operatively provided by the absorbent composite 32. Leg openings, which are provided at the laterally opposed side margins of the of the intermediate portion of the article, may be elasticized with leg elastics. A fastening system, such as a system including fasteners 36, is configured to provide a back-to-front fastening in which the back waistband portion 12 can be arranged in an overlapping relation with the front waistband portion 14 to thereby encircle the wearer's body and hold the diaper secure on the wearer during use. Optionally, the fastening system can employ fastener tabs 36 which are configured to provide a front-to-back fastening which arranges and joins the front waistband portion 14 in an overlapping relation with the back waistband portions 12 to thereby encircle the wearer's body during use.

As representatively shown, the front waistband section 14 of the diaper 10 has a laterally opposed, front pair of side edge regions 88, and the rear waistband section 12 has a laterally opposed, rear pair of side edge regions 86. The intermediate section 16 interconnects the front and rear waistband section and provides a diaper crotch region which is typically positioned between the legs of the wearer. The article may have an appointed fastener landing zone 50 which is disposed on the outward surface of the article. The landing zone may be integrally formed with a selected component, such as the backsheet layer 30, the extensible outer cover layer 40, or the second body panel 53. As representatively shown in FIGS. 1A and 1C, the landing zone 50 may alternatively be a separately provided member which is, for example, disposed on the outward surface of the backsheet layer 30. The liquid permeable topsheet layer 28 is superposed in facing relation with the backsheet layer 30, and the appointed retention portion 48 of the absorbent structure is operably connected and affixed between the backsheet layer 30 and topsheet layer 28. In particular arrangements, the topsheet layer 28 and the retention portion 48 can be constructed to be substantially nonelastomeric and can be operatively attached to the backsheet member 30 to substantially restrain excessive stretching of the backsheet member.

FIGS. 1, 2 and 3 show typical plan views of the representative disposable diaper 10 in its generally flat-out, mostly uncontracted state (i.e., with substantially all of the freely stretchable, elastomerically induced gathering and contraction removed, except where the gathers have been operatively restrained from re-expanding). More particularly, FIGS. 1, 2 and 3 show the bodyside surface of the diaper, which is intended to contact the wearer, facing the viewer. The outer edges of the diaper define a periphery 18 with laterally opposed, longitudinally extending side edge margins or regions 20; and longitudinally opposed, laterally extending end edge margins or regions 22. The side edges define leg openings for the diaper, and optionally, are curvilinear and contoured. The end edges are shown as straight, but optionally, may be curvilinear.

With regard to the designated surfaces of the article and components, the various inward or bodyside surfaces are configured to face toward the body of the wearer when the article is placed about the wearer for ordinary use. The various outward surfaces are configured to face away from the wearer's body when the article is placed about the wearer.

The diaper 10 typically includes a porous, substantially liquid permeable topsheet 28; a substantially liquid impermeable backsheet 30; a retention portion 48 positioned and connected between the topsheet and backsheet; a surge management portion 46 located operatively adjacent to the retention portion; and a system of elastomeric gathering members. The system of elastomeric gathering members can, for example, include leg elastics 34 and optional waist elastics 43, and the surge management portion 46 is positioned in a liquid communication with at least one major facing surface of the retention portion 48. The topsheet 28, backsheet 30, retention portion 48, surge management portion 46, leg elastics 34, and any waist elastics or other elastomeric members may be assembled together into a variety of well-known diaper configurations. The diaper can additionally include a system of containment flaps (not shown), and a system of side panel or ear region members 38, which may be elasticized or otherwise rendered elastomeric.

Examples of articles which include elasticized side panels and selectively configured fastener tabs are described in U.S. patent application Ser. No. 168,615 of T. Roessler et al., entitled DYNAMIC FITTING DIAPER, and filed Dec. 16, 1993 Various techniques for forming the desired fastening systems are described in U.S. Pat. No. 5,399,219 of T. Roessler et al., entitled METHOD FOR MAKING A FASTENING SYSTEM FOR A DYNAMIC FITTING DIAPER and issued Ma. 21, 1995; in U.S. patent application Ser. No. 286,086 of D. Fries, entitled A PROCESS FOR ASSEMBLING ELASTICIZED EAR PORTIONS and filed Aug. 3, 1994 which corresponds to U.S. Pat. No. 5,540,796; and in U.S. patent application Ser. No. 08/415,383 of D. Fries, entitled AN ASSEMBLY PROCESS FOR A LAMINATED TAPE and filed Apr. 3, 1995 which corresponds to U.S. Pat. No. 5,595,618. The disclosures of the above-described documents are incorporated herein by reference in a manner that is consistent (not in conflict) herewith.

Diaper 10 generally defines the longitudinally extending length dimension 26 and the laterally extending width dimension 24, as representatively shown in FIG. 1. The diaper may have any desired shape, such as rectangular, I-shaped, a generally hourglass shape, or a T-shape. With the T-shape, the crossbar of the "T" may comprise the front waistband portion of the diaper, or may alternatively comprise the rear waistband portion of the diaper.

The topsheet 28 and backsheet 30 may be generally coextensive (e.g. FIG. 1), and optionally, may be non-coextensive (FIG. 2). Either or both of the topsheet 28 and backsheet 30 may have length and width dimensions which are generally larger than those of the retention portion 48 and extend beyond the corresponding dimensions of the retention portion 48 to provide edge margins or regions 20 and 22. Where the article includes the absorbent composite 32, either or both of the topsheet 28 and backsheet 30 may have length and width dimensions which extend beyond the corresponding dimensions of the retention portion 48 to provide end edge margins or regions 78 and 79, and side edge margins or regions 20 of the absorbent composite 32 (e.g. FIG. 3). In particular aspects, the side edge margins of the absorbent composite can be configured to provide at least a portion of the side regions 20 of the article. As representatively shown in FIGS. 3 and 3A, for example, the side margins of the absorbent composite 32 can provide the article side margins along the intermediate portion 16 of the article.

The topsheet 28 is operatively associated with and superimposed on backsheet 30, thereby defining the periphery of the diaper. The waistband regions comprise those portions of the diaper, which when worn, wholly or partially cover or encircle the waist or mid-lower torso of the wearer. In the representatively shown configurations, the first and second body panels 52 and 53 are arranged to provide the back and front waistband regions 12 and 14, respectively. The intermediate, crotch region 16 of the article lies between and interconnects the waistband regions 14 and 12, and comprises that portion of the diaper which, when worn, is positioned between the legs of the wearer and covers the lower torso of the wearer. Thus, the intermediate crotch region 16 is an area where repeated liquid surges typically occur in the diaper or other disposable absorbent article.

The backsheet 30 can typically be located along an outward-side surface of the absorbent retention portion 48 and may be composed of a liquid permeable material, but desirably comprises a material which is configured to be substantially impermeable to liquids. For example, a typical backsheet can be manufactured from a thin plastic film, or other flexible, substantially liquid-impermeable material. As used in the present specification, the term "flexible" refers to materials which are compliant and which will readily conform to the general shape and contours of the wearer's body.

The backsheet 30 prevents the exudates contained in the absorbent composite 32 from wetting articles, such as bedsheets and overgarments, which contact diaper 10. In particular embodiments of the invention, the backsheet 30 can include a film, such as a polyethylene film, having a thickness of from about 0.012 millimeters (0.5 mil) to about 0.051 millimeters (2.0 mils). For example, the backsheet film can have a thickness of about 1.25 mil.

Alternative constructions of the backsheet may comprise a woven or nonwoven fibrous web layer which has been totally or partially constructed or treated to impart the desired levels of liquid impermeability to selected regions that are adjacent or proximate the absorbent composite. For example, the backsheet may include a gas-permeable, nonwoven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene cast film and a 0.7 ounce per square yard (23.8 gsm) polypropylene spunbond material (2 denier fibers). A material of this type has been employed to form the outercover of a HUGGIES ULTRATRIM diaper, which has been commercially available from Kimberly-Clark Corporation. The backsheet 30 typically provides the outer cover of the article, and the nonwoven fabric layer typically provides the outward surface of the article. Optionally, however, the article may include a separate outer cover component member 40 which is additional to the backsheet.

The backsheet 30 may include a micro-porous, "breathable" material which permits gases, such as water vapor, to escape from the absorbent composite 32 while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In the various configurations of the invention, where a component, such as the backsheet 30 or the containment flaps are configured to be permeable to gas while having a resistance and limited permeability to aqueous liquid, the liquid resistant component can have a construction which is capable of supporting a selected hydrohead of water substantially without leakage therethrough. A suitable technique for determining the resistance of a material to liquid penetration is Federal Test Method Standard FTMS 191 Method 5514, 1978, or an equivalent thereof.

The backsheet member 30 is sufficiently impermeable liquid and semi-liquid materials to substantially prevent the undesired leakage of waste materials, such as urine and feces, during ordinary use. In particular arrangements, the backsheet member can desirably support a hydrohead of at least about 45 centimeters (cm) substantially without leakage. The backsheet member 30 can alternatively support a hydrohead of at least about 55 cm, and optionally, can support a hydrohead of at least about 60 cm, or more, to provide further protection against excessive leakage.

The size of the backsheet 30 is typically determined by the size of absorbent composite 32 and the particular diaper design selected. Backsheet 30, for example, may have a generally T-shape, a generally I-shape or a modified hourglass shape, and may extend beyond the terminal edges of the retention portion 48 by a selected distance, such as a distance within the range of about 1.3 centimeters to 2.5 centimeters (about 0.5 to 1.0 inch), to provide at least a portion of the side and end margins.

The topsheet 28 presents a body-facing surface which is compliant, soft-feeling, and non-irritating to the wearer's skin. Further, the topsheet 28 can be less hydrophilic than absorbent composite 32, and is sufficiently porous to be liquid permeable, permitting liquid to readily penetrate through its thickness to reach the absorbent composite. A suitable topsheet layer 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet layer 28 is typically employed to help isolate the wearer's skin from liquids held in the absorbent composite 32.

Various woven and nonwoven fabrics can be used for topsheet 28. For example, the topsheet may be composed of a meltblown or spunbonded web of the desired fibers, and may also be a bonded-carded-web. The various fabrics can be composed of natural fibers, synthetic fibers or combinations thereof.

For the purposes of the present description, the term "nonwoven web" means a web of fibrous material which is formed without the aid of a textile weaving or knitting process. The term "fabrics" is used to refer to all of the woven, knitted and nonwoven fibrous webs.

The topsheet fabrics may be composed of a substantially hydrophobic material, and the hydrophobic material may optionally be treated with a surfactant or otherwise processed to impart a desired level of wettability and hydrophilicity. In a particular embodiment of the invention, topsheet 28 is a nonwoven, spunbond polypropylene fabric composed of about 2.8–3.2 denier fibers formed into a web having a basis weight of about 22 gsm and density of about 0.06 gm/cc. The fabric can be surface treated with an operative amount of surfactant, such as about 0.28% Triton X-102 surfactant. The surfactant can be applied by any conventional means, such as spraying, printing, brush coating or the like.

The topsheet 28 and backsheet 30 are connected or otherwise associated together in an operable manner. As used herein, the term "associated" encompasses configurations in which topsheet 28 is directly joined to backsheet 30 by affixing topsheet 28 directly to backsheet 30, and configurations wherein topsheet 28 is indirectly joined to backsheet 30 by affixing topsheet 28 to intermediate members which in turn are affixed to backsheet 30. Topsheet 28 and backsheet 30 can, for example, be joined to each other in at least a portion of the diaper periphery by attachment mechanisms (not shown) such as adhesive bonds, sonic bonds, thermal bonds, pinning, stitching or any other attachment techniques known in the art, as well as combinations thereof. For example, a uniform continuous layer of adhesive, a patterned layer of adhesive, a sprayed pattern of adhesive or an array of separate lines, swirls or spots of construction bonds may be used to affix the topsheet 28 to the backsheet 30. It should be readily appreciated that the abovedescribed attachment mechanisms may also be employed to suitably interconnect, assemble and/or affix together the various other component parts of the articles which are described herein.

The absorbent body or composite employed in the article provides an absorbent structure which includes a retention portion 48 for holding and storing absorbed liquids and other waste materials. For example, the retention portion can include an absorbent pad composed of selected hydrophilic fibers and high-absorbency particles. The absorbent composite is positioned and sandwiched between the topsheet 28 and backsheet 30 to form the diaper 10. The absorbent composite has a construction which is generally compressible, conformable, non-irritating to the wearer's skin, and capable of absorbing and retaining body exudates. It should be understood that, for purposes of this invention, the absorbent composite structure may comprise a single, integral piece of material, or alternatively, may comprise a plurality of individual separate pieces of material which are operably assembled together.

Various types of wettable, hydrophilic fibrous material can be used to form the component parts of absorbent composite 32 particularly the retention portion 48. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonweftable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with such system, fibers having contact angles less than 90° are designated "wettable", while fibers having contact angles greater than 90° are designated "nonwettable".

The absorbent structure of the article (e.g. the absorbent composite 32) can include a retention portion 48 having a matrix of hydrophilic fibers, such as a web of cellulosic fluff, mixed with particles of high-absorbency material. In particular arrangements, the retention portion 48 of the absorbent structure may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent composite and relatively higher concentrations toward the outside of the absorbent structure. Suitable z-gradient configurations are described in U.S. Pat. No. 4,699,823 entitled A NON-LAYERED ABSORBENT INSERT HAVING A Z-DIRECTIONAL SUPERABSORBENT CONCENTRATION GRADIENT by Kellenberger et al., which was issued Oct. 13, 1987, the entire disclosure of which is incorporated herein by reference in a manner that is consistent (not in conflict) with the present description. Alternatively, the concentrations of superabsorbent particles may be arranged in a non-step-wise gradient, through a substantial portion of the thickness (z-direction) of the absorbent structure, with higher concentrations toward the bodyside of the absorbent composite and relatively lower concentrations toward the outside of the absorbent structure. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent composite include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in absorbent retention portion 48 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in absorbent retention portion 48. Desired for use are particles having an average size of from about 20 microns to about 1 millimeter.

"Particle size" as used herein means the weighted average of the smallest dimension of the individual particles.

The hydrophilic fibers and high-absorbency particles can be configured to form an average composite basis weight which is within the range of about 400–900 gsm. In certain aspects of the invention, the average composite basis weight is within the range of about 500–800 gsm, and alternatively is within the range of about 550–750 gsm to provide desired performance.

To improve the containment of the high-absorbency material, absorbent structure of the article can include an overwrap, such as wrap sheet 74, which is placed immediately adjacent and around the retention portion 48, and may be bonded to the absorbent structure and to the various other components of the article. The wrap sheet is preferably a layer of absorbent material which covers the major bodyside and outerside surfaces of the retention portion, and preferably encloses substantially all of the peripheral edges of the retention portion to form a substantially complete envelope thereabout. Alternatively, the wrap sheet can provide an absorbent wrapping which covers the major bodyside and outerside surfaces of the retention portion, and encloses substantially only the lateral side edges of the retention portion. Accordingly, both the linear and the inwardly curved portions of the lateral side edges of the wrap sheet would be closed about the retention portion. In such an arrangement, however, the end edges of the wrap sheet may not be completely closed around the end edges of the absorbent composite at the waistband regions of the article.

For example, the complete wrap sheet 74, or at least the bodyside layer of the wrap sheet, may comprise a meltblown web composed of meltblown fibers, such as meltblown polypropylene fibers. Another example of the absorbent wrap 74 may comprise a low porosity cellulosic web, such as a tissue composed of an approximately 50/50 blend of hardwood/softwood fibers.

The absorbent wrap 74 may comprise a multi-element wrapsheet which includes a separate bodyside wrap layer and a separate outerside wrap layer, each of which extends past all or some of the peripheral edges of the retention portion 48. Such a configuration of the wrap sheet can, for example, facilitate the formation of a substantially complete sealing and closure around the peripheral edges of the retention portion 48. In the back waistband portion of the illustrated diaper, the absorbent wrap may also be configured to extend an increased distance away from the periphery of the retention portion to add opacity and strength to the back side-sections of the diaper. In the illustrated embodiment, the bodyside and outerside layers of absorbent wrap 74 can extend at least about ½ inch beyond the peripheral edges of the retention portion to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 74 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearers skin, and the high porosity, lower basis weight outerside layer can help reduce costs.

The diaper 10 can also include a surge management layer 46 which helps to decelerate and diffuse surges of liquid that may be introduced into the absorbent structure of the article. The surge layer 46 can also temporarily hold the liquid for a limited period of time, spread and direct the distribution of the liquid, and then release the liquid for absorption into the retention portion 48. In the illustrated embodiment, for example, the surge layer 46 can be located on an inwardly facing body side surface of the topsheet layer 28. Alternatively, the surge layer 46 may be located adjacent to an outer side surface of the topsheet 28 to be interposed between the topsheet 28 and the retention portion 48. Examples of suitable surge management layers 46 are described in U.S. patent application Ser. No. 206,986 of C. Ellis and D. Bishop, entitled FIBROUS NONWOVEN WEB SURGE LAYER FOR PERSONAL CARE ABSORBENT ARTICLES AND THE LIKE, filed Mar. 4, 1994 which corresponds to U.S. Pat. No. 5,486,166; and U.S. patent application Ser. No. 206,069 of C. Ellis and R. Everett, entitled IMPROVED SURGE MANAGEMENT FIBROUS NONWOVEN WEB FOR PERSONAL CARE ABSORBENT ARTICLES AND THE LIKE, filed Mar. 4, 1994 which corresponds to U.S. Pat. No. 5,490,846; the entire disclosures of which are hereby incorporated by reference in a manner that is consistent herewith.

With reference again to FIGS. 3 through 3F where the article includes body panels 52 and/or 53, the first body panel 52 is desirably a separately provided member which is attached to and extends across the inwardly facing, bodyside surface of the first end region 78 of the absorbent composite. The first body panel can be joined to the absorbent composite and arranged to provide the back waistband portion 12 of the article. Alternatively, the first body panel 52 may be joined to the absorbent composite and arranged to provide the front waistband portion 14 of the article. In desired configurations, the first body panel 52 can have a longitudinally outboard terminal end edge 60 which is substantially coterminous with a first, longitudinally terminal, end edge of the article. The absorbent composite 32 is attached to extend across and span over an outward surface 56 of the first body panel 52. As representatively shown, the first body panel 52 can be joined to provide the back waistband portion 12 of the article, and a second body panel 53 can be joined to a longitudinally opposed end of the absorbent composite 32 to provide the front waistband portion 14 of the article.

The second body panel 53 can also be a separately provided member, which is attached to extend across the bodyside surface of the second end region 79 of the absorbent composite. The second body panel 53 has a longitudinal panel length 59 which is less than the article length 26, and the second body panel is longitudinally spaced away from the first body panel 52. In desired configurations, the second body panel 53 can have a longitudinally outboard terminal end edge 61 which is substantially coterminous with a second, longitudinally terminal, end edge of the article. The absorbent composite 32 is attached to extend across and span over an outward surface 56 of the second body panel 53, and as representatively shown, the absorbent composite can operatively extend to interconnect and span between the first and second body panels.

Each body panel 52 and 53 can have a desired shape, which may be generally rectangular, or may have a non-rectangular, contoured shape. As representatively shown, each body panel can extend longitudinally past its corresponding end edge of the topsheet layer 28 and/or can extend laterally beyond its corresponding end edge of the backsheet layer 30. Optionally, either or both body panels can have longitudinally outboard edges which are substantially coterminous with their corresponding end edges of the topsheet layer 28 ardor backsheet layer 30. Laterally opposed, side-end sections of the body panel can extend transversely beyond the side edges of the absorbent composite 32 to provide extending ear portions 38 of the article. Accordingly, each body panel can extend across substantially the entire cross-directional width of its corresponding waistband portion of the article. Each body panel can extend laterally beyond the side edges of the topsheet layer 28 and/or can extend laterally beyond the side edges of the backsheet layer 30. In particular arrangements, the body panel can be configured with lateral end sections which have a tapered shape to provide tapered ear portions. Each tapered ear portions can have a relatively longer longitudinal length adjacent the side margins of the absorbent composite, and a relatively shorter longitudinal length at the laterally distal ends of the ear portion.

In desired arrangements, at least a medial portion 64 of the laterally extending and longitudinally inboard edge 62 of the first body panel 52 can be substantially unattached to bodyside surface of the absorbent composite 32. Similarly, the second body panel 53 can have a longitudinally inboard terminal end edge 63, and at least a medial portion 65 of the end edge 63 can be substantially unattached to the absorbent composite 32. Either or both of the inboard edges may be substantially straight or curved, as desired. In particular aspects, at least a portion of the inboard edge of either or both of the body panels 52 and 53 can be arranged in a configuration which is concave-inboard, as illustrated in FIG. 3 . As representatively shown, the appointed concave curvature can commence at each side margin of the absorbent composite, and can traverse generally laterally across the absorbent composite with a middle portion of the curvature displaced toward the longitudinal end of the article. The curvature can help provide an improved conformance of the body panel with the contours of the wearer's body.

In other aspects of the invention, the first longitudinally terminal end edge 82 of substantially the entire absorbent composite 32 can be spaced relatively inboard from the longitudinally outboard, terminal end edge 60 of the first body panel 52. Accordingly, the body panel can extend longitudinally past and project length-wise beyond its corresponding, generally adjacent, terminal end edge 82 of the absorbent composite. Similarly, the second longitudinally terminal end edge 83 of substantially the entire absorbent composite 32 can be spaced relatively inboard from the longitudinally outboard, terminal end edge 61 of the second body panel 53. Accordingly, the second body panel can extend longitudinally past and project length-wise beyond its corresponding, generally adjacent, terminal end edge 82 of the absorbent composite.

As representatively shown in FIGS. 3 through 3B, a corresponding, expandable attachment section 92 can be provided along at least a portion of each associated side region 20 of the absorbent composite 32 in the first end region 78 of the absorbent composite. Each expandable attachment section can be expandable at least outwardly or at least along the lateral cross-direction of the article width 24, and each expandable attachment section can be configured to secure its correspondingly joined side edge region of the absorbent composite to the outward surface 56 of the first body panel 52.

Similarly, a corresponding, expandable attachment section 92 can be provided along at least a portion of each associated side region 20 of the absorbent composite 32 in the second end region 79 of the absorbent composite. Each expandable attachment section can be expandable at least outwardly or at least along the lateral cross-direction of the article width 24, and each expandable attachment section can be configured to secure its correspondingly joined side edge region of the absorbent composite to the outward surface 56 of the second body panel 53.

During the conditions of ordinary use, the expandable attachment sections 92 can advantageously allow and provide for a controlled expansion of the volume of the absorbent composite 32, especially after the absorbent composite has started absorbing liquids. In the various configurations of the invention, each expandable attachment section may be a separately provided member which is assembled into the article, or may be integrally formed from appointed portions of other existing components of the article. For example, the expandable attachment section may be formed from appointed portions of the backsheet 30, topsheet 28 or operative combinations thereof. In particular aspects of the invention, the various expandable attachment sections can be substantially free of absorbent materials, such as hydrophilic fiber and superabsorbent polymers. Optionally, the various expandable attachment sections can include a selected quantity of absorbent materials.

Examples of absorbent articles having an absorbent composite attached to body panels with expandable attachment sections are described in U.S. patent application Ser. No. 091250,470 entitled A DISPOSABLE GARMENT HAVING DRYNESS BARRIERS WITH EXPANDABLE ATTACHMENT TO AN ABSORBENT by P. T. VanGompel et al., which was filed Feb. 12, 1999

The entire disclosure of this document is incorporated herein by reference in a manner that is consistent herewith.

In the representatively shown configuration, the expandable attachment section 92 has the arrangement of a z-fold. In optional configurations, the expandable attachment section 92 of the article may, for example, include at least one C-folded, or otherwise C-turned member or portion, and the C-turned portion can be provided at each side margin region 20 of the absorbent composite 32. Examples of articles having an absorbent composite with C-turned side margins are described in U.S. patent application Ser. No. 09/250471 entitled THREE-DIMENSIONAL, INWARD LEG GATHER DISPOSABLE GARMENT by P. T. VanGompel et al., which was filed Feb. 12, 1999. The entire disclosure of this document is incorporated herein by reference in a manner that is consistent herewith.

Each expandable attachment section 92 can be bonded or otherwise affixed to its correspondingly associated region of the body panel with an operative side securement 42. Each side securement 42 may be substantially continuous or discontinuous, and may be distributed randomly or in a selected area pattern.

Additionally, each body panel attachment 42 can be located proximate a longitudinally extending, terminal side edge 81 of its corresponding side margin 20.

The article of the invention can further include a first, laterally extending, end attachment 44 which is distributed along at least a portion of the first end region 78 of the absorbent composite 32 to help secure the end of the absorbent composite to the body panel 52. The end attachment 44 may also be configured to provide a sealing, liquid-barrier attachment which can help resist a passage of liquid between the absorbent composite and the outward surface 56 of the first body panel 52. Similarly, a second laterally extending end attachment 44 can be distributed along at least a portion of the second end region 79 of the absorbent composite 32 to secure the second end of the absorbent composite to the second body panel 53, and to help resist a passage of liquid between the absorbent composite and the outward surface 56 of the second body panel 53.

The side securements 42 and end attachments 44 can be provided by various suitable mechanisms. For example, each of the side securements 42 and end attachments 44 may include adhesive bonds, thermal bonds, ultrasonic bonds, pins, staples, or the like, as well as combinations thereof.

In the representatively shown configuration, each end attachment 44 is provided by a plurality of individually spaced apart, thermal or ultrasonic bonds arranged in a selected pattern. The pattern bond may be regular or irregular in distribution, and is operatively configured to provide the desired securement, expandability and/or leakage resistance in the article. Each end attachment 44 may alternatively include a laterally extending bond which is substantially continuous along a major portion of the lateral width of the absorbent composite. Similarly, each side securement 42 may include a longitudinally extending bond which is substantially continuous along a major portion of the longitudinal length of the article portion at which each expandable attachment section is operably affixed to its corresponding, associated body panel.

In particular aspects of the invention, either or both of the body panels 52 and 53 may be composed of a wide range of materials with various basis weights and properties. For example, the body panel material may include knitted or other woven fabrics, nonwoven fabrics, polymer films, laminates, and the like, as well as combinations thereof. It should be readily appreciated that each of the individual body panels may be composed of different materials, or of substantially the same material.

In the various configurations of the invention, the body panel material may be substantially permeable to air or substantially impermeable to air. The body panel material also may be substantially liquid-permeable or substantially liquid-impermeable. In particular arrangements, the body panel material may be substantially nonelastomeric. In other aspects, the body panels 52 and/or 53 can include an elastomeric material which is elastomerically stretchable at least along the lateral article width 24. Examples of such elastomeric materials can include a neck-bonded-laminate (NBL), a stretch-bonded-laminate (SBL), a necked-thermal laminate, or the like, as well as combinations thereof. Such laminates can provide an improved combination of cloth-like feel and elastomeric stretchability.

With reference to FIG. 3, the first body panel 52 and/or the second body panel 53 can have a longitudinal length 58, 59 which is not more than a maximum of about 80% of the article length 26. Alternatively, either or both body panels can alternatively have a longitudinal length which is not more than about 65% of the article length 26, and optionally, is not more than about 50% of the article length to provide improved benefits. In desired arrangements, the longitudinal length of the body panel can be not more than about 40%. In further arrangements, the longitudinal length of the body panel can be not more than about 35%, and optionally not more than about 30% of the article length to provide improved performance.

In other aspects of the invention, the first body panel 52 and/or the second body panel 53 can have a longitudinal length which is at least a minimum of about 5% of the article length 26. Alternatively, at least one of the body panels (or both) can have a longitudinal length which is at least about 10% of the article length, and optionally, is at least about 15% of the article length to provide improved performance. Desirably, at least one of the body panels, particularly the back body panel, can have a longitudinal length which is at least about 2 cm. More desirably the selected body panel can have a longitudinal length which is at least about 4 cm, and optionally, is at least about 6 cm to provide improved fit and skin dryness.

In the various configurations of the invention, the absorbent article can further include at least one elastomeric member attached to provide an operative, longitudinally extending, leg elastic member 34. Each of the leg elastic members 34 can be operatively attached to an inward or outward surface of at least a portion of the lateral side edge regions 20 of the article. In the various configurations of the invention, each elastomeric member can be secured to an outward surface of the backsheet layer 30. Where the article includes the outer cover layer 40, each elastomeric member can be sandwiched and attached between the outer cover layer and the backsheet layer 30. The elastomeric members can alternatively be sandwiched and secured between the backsheet layer 30 and topsheet layer 28, and can optionally be attached to the bodyside surface of the topsheet layer. It should be readily appreciated that any of the conventional attaching mechanisms described in the present disclosure may be employed to secure the leg elastic members into the article. In the representatively shown arrangement, the attachment mechanism can include a distributed pattern of sonic bonds.

The elastic members 34 may have any of a multitude of configurations. For example, the overall width of the individual elastic members 34 may be varied from about 0.25 mm (about 0.01 inch) to about 25 mm (about 1 inch) or more. The elastic members may comprise a single strand of elastic material, or may comprise several parallel or non-parallel strands 98 of elastic material and the elastic members may be applied in a rectilinear or curvilinear arrangement. Where the strands are non-parallel, two or more of the strands may intersect or otherwise interconnect within the elastic member. In particular arrangements, the elastic members may include elastomeric strands 98 which are optionally located and laminated between the topsheet layer 28 and backsheet layer 30 of the absorbent composite 32. The elastic members may be affixed to the diaper in any of several ways which are known in the art. For example, the elastic members may be ultrasonically bonded, heat and pressure sealed using a variety of bonding patterns, or adhesively bonded to the diaper 10 with sprayed or swirled patterns of hotmelt adhesive.

Each of the leg elastic members 34 may optionally be a composite which includes at least one carrier layer, such as a fabric layer, and a plurality of elastomeric strands 98 that are operatively attached to the carrier layer. Various mechanisms, such as adhesive, thermal bonds, sonic bonds, or the like as well as combinations thereof, can be employed to provide the desired attachments between the elastomeric strands 98 and the leg elastic carrier layer. For example, each leg elastic member may be a laminate composed of a plurality of elastomeric strands sandwiched and held between a pair of carrier layers. Each carrier layer may be composed of a woven or nonwoven fabric having a basis weight within the range of about 10–50 g/m$^2$, but may optionally be composed of a polymer film material. The carrier layers may be composed of a polypropylene spun-bond nonwoven fabric, and the pair of carrier layers may be adhesively bonded together with a suitable pattern of adhesive, such as a swirl-pattern of pressure-sensitive adhesive.

Where the leg elastic members 34 include a carrier layer or sheet to which are attached a grouped set of elastics composed of a plurality of individual elastic strands, the elastic strands may intersect or be interconnected, or be entirely separated and spaced from each other. The carrier layer may, for example, comprise a 0.002 cm thick polymer film, such as a film of unembossed polypropylene material. The elastic strands can, for example, be composed of LYCRA elastomer available from DuPont, a business having offices in Wilmington, Del. Each elastic strand is typically within the range of about 470–1500 decitex (dtx), and may be about 940–1050 dtx. In particular embodiments of the invention, for example, three or four strands can be employed for each elasticized legband.

In the various configurations of the invention, the leg elastics 34 may be generally straight or optionally curved. For example, the curved elastics can be inwardly bowed toward the longitudinal centerline of the diaper. In particular arrangements, the curvature of the elastics may not be configured or positioned symmetrically relative to the lateral centerline of the diaper. The curved elastics may have an inwardly bowed and outwardly bowed, reflex-type of curvature, and the length-wise center of the elastics may optionally be offset by a selected distance toward either the front or rear waistband of the diaper to provide desired fit and appearance. In particular embodiments of the invention, the innermost point (apex) of the set of curved elastics can be offset towards the front or rear waistband of the diaper, and the outwardly bowed reflexed-portion can be positioned toward the diaper front waistband.

With reference to FIGS. 1D, 1F and 2C, a restraint 84 can be applied to an intermediate crotch portion of each side margin of the article to operatively restrict a re-expansion of the constrained section 94 of the gathers 66 located in the portion of each side margin that is positioned in the intermediate region of the article. Either side margin and preferably both side margins 20 of the absorbent structure of the article (e.g. the absorbent composite 32) can include a restraint 84 applied and affixed to an appointed portion of the gathers 66 in each side margin. In particular aspects, each restraint 84 can be configured to substantially prevent a re-expansion of its associated and corresponding, constrained section 94 of the gathers 66 in its corresponding side margin of the article.

A particular aspect of the invention can have a configuration wherein each constrained section 94 of the gathers 66 in the side margins 20 is offset toward an appointed back waistband portion of the article. In further aspects, each constrained section 94 of the gathers 66 in the side margins can advantageously be located approximately adjacent a juncture between the intermediate portion of its corresponding side margin and a laterally outward extending ear portion 38 of the article. Such a location of the constrained sections can provide improved appearance and can position the constrained sections away from the areas of the wearer's legs that are more susceptible to excessive rubbing and irritation.

As representatively shown, each restraint 84 can be provided by an area of inter-attachment within its corresponding set of gathers 66. In particular, the restraint 84 can include a region of inter-attachment between an appointed set of individual gathers. In the example of the shown configuration, a system of restraints are operatively applied to the outer cover layer 40. The restraints can alternatively be applied to the backsheet layer, the topsheet layer or directly to the associated elastomeric members, as well as combinations of the various materials present in the corresponding set of gathers.

In particular configurations, the restraint 84 can be provided by an adhesive, a system of thermal bonds, a system of sonic bonds and the like, as well as combinations thereof. In is further aspects, the restraint 84 can include a separately provided mechanical attachment, such as stitching, stapling, pinning or the like, as well as combinations thereof. The restraint may be arranged in a regular or irregular pattern, or may have a discontinuous or substantially continuous configuration, as desired In further aspects, the restraint 84 can include a separately provided holder member 90 which can be configured and employed to provide each constrained section 94 of an appointed, corresponding set of the gathers 66, as representatively shown in FIGS. 1G, 2F and 3F. The separately provided holder member 90 can be attached to a limited portion of the gathers 66 to provide the desired restraint 84 in each constrained section 94.

The holder member 90 can, for example, be composed of a woven fabric, a nonwoven fabric, a film or the like, as well as combinations thereof. In desired configurations, the holder member 90 can be composed of a synthetic nonwoven fabric, such as a polypropylene spunbond fabric.

The holder member can be directly attached or indirectly attached to the appointed portions of its corresponding leg elastic member 34. For example, the holder member may be attached to a bodyside surface of the topsheet layer 28, an outward side surface of the topsheet layer, an inward side surface of the backsheet layer 30, an outward side surface of the backsheet layer, or may be sandwiched between the topsheet and backsheet layers of the article.

In desired configurations, the holder member can be substantially nonelastomeric. Additionally, the holder member 90 can be substantially non-extensible. The degree of non-extensibility can, for example, be determined in accordance with the techniques described herein with respect to the restraint 84 and the constrained section 94.

The size and configuration of each restraint 84 can affect the size and configuration of its corresponding constrained section 94. To provide operational effectiveness, each constrained section can desirably have an operative extent along its relatively longer, lengthwise dimension which is at least a minimum of about 10 mm. The lengthwise extent of the constrained section can alternatively be at least about 20 mm, and optionally, can be at least about 30 mm to provide improved performance. In other aspects, the lengthwise extent of the constrained section can be up to a maximum of about 70 mm, or more. The lengthwise extent of the constrained section can alternatively be up to about 60 mm, and optionally, can be up to about 50 mm to provide improved effectiveness.

Additionally, each constrained section can have an operative extent along its relatively shorter, crosswise dimension which is at least a minimum of about 0.3 mm. The crosswise extent of the constrained section can alternatively be at least about 2 mm, and optionally, can be at least about 5 mm to provide improved performance. In other aspects, the crosswise extent of the constrained section can be not more than a maximum of about 25 mm. The crosswise extent of the constrained section can alternatively be not more than about 18 mm, and optionally, can be not more than about 12 mm to provide improved benefits.

If the dimensions of the restraint and/or constrained section are too small, then the difference in length between the restrained side margins and the relatively unrestrained medial portion of the article does not adequately provide the desired 3-dimensional, pocket shape to the article. If the dimensions of the restraint and/or constrained section are too large, then the restrained length of the article will be too short and will provide poor fit.

In still other aspects, each restraint 84 and its corresponding constrained section 94 can provide a reduced length 96 of each constrained side margin of the article when the article is stretched and extended for ordinary placement on the wearer. The reduced article length can be a distance which is a minimum of at least about 2% less than the original, fully extended, unconstrained length of the article, such as provided by the unconstrained medial portions of the article that are located laterally between the article side margins. The reduced article length can alternatively be at least about 4% less, and optionally, can be at least about 6% less than the original, full article length to provide improved performance. Accordingly, the reduced length of the article side margin can be not more than about 98% of the original, full article length. Alternatively, the reduced article length can be not more than about 96%, and optionally, not more than about 94% of the original, full article length to provide improved benefits.

In other aspects, the reduced article length can be not more than a maximum of about 15% less than the original, fully extended article length. The reduced article length can alternatively be not more than about 12% less, and optionally, can be not more than about 10% less than the original, full article length to provide improved performance. Accordingly, the reduced length of the article side margin can be not less than about 85% of the original, full article length. Alternatively, the reduced article length can be not less than about 88%, and optionally, not less than about 90% of the original, full article length to provide improved benefits.

If the percentage of reduction in the length article side margin is too small, then the difference in length between the restrained side margins and the relatively unrestrained medial portion of the article does not adequately provide the desired 3-dimensional, pocket shape to the article. If the percentage of reduction in the length of the article margin is too large, then the operative length of the restrained side margin will be too short and will provide poor fit.

A suitable technique for calculating the percentage of the reduction in length from the original extended longitudinal length of each side margin is represented by the following:

Percentage of reduction in length (%)=100*(Lu−Lr)/Lu; where:

Lu=original, unrestrained, fully extended length of the article along the longitudinal or lateral direction, whichever direction corresponds to gathering direction of the side margin being assessed; and Lr=reduced length of such side margin along the same longitudinal or lateral direction, respectively, when the foreshortened, restrained side margin is extended-to-stop at its maximum constrained length.

In still further aspects, each constrained section 94 can exhibit a lengthwise extension which is not more than about 6 mm, when subjected to a tensile force of 200 grams/inch (0.77 Newtons/cm), as determined along the expansion direction of its associated gathers. Alternatively, the lengthwise extension can be not more than about 4 mm, and optionally, can be not more than about 2 mm to provide improved performance.

Another aspect of the invention, can have a configuration wherein each constrained section 94 can exhibit a lengthwise extension which is not more than about 8% when subjected to the tensile force of 200 g/in (0.77 N/cm), as determined along the expansion direction of its associated gathers. Alternatively, each constrained section 94 can exhibit a lengthwise extension which is not more than about 5%, and optionally, is not more than about 2% to more effectively provide the desired benefits.

By employing the described amounts of extension in the constrained section, the constrained length is better able to provide the length difference (e.g. Lu−Lr), and the localized resistance to stretching that better cooperate to produce the desired threedimensional pocket shape to the article. A suitable technique for generating a representative tensile-load vs. extension curve to determine the effect of a restraint on the tensile behavior of a constrained section is set forth hereinbelow in the "Examples".

With reference to FIGS. 1B and 2A, particular aspects of the invention can have a configuration wherein each elastomeric member 34 can include a plurality of elastomeric strands 98. In further aspects, each constraint 84 can be configured to operate on substantially all of the elastomeric strands 98. In other aspects, each restraint 84 can be configured to operate on less than all of the elastomeric strands. For example, each restraint 84 can have a cross-directional extent which intersects less than all of the elastomeric strands 98. Accordingly, in a similar manner, the corresponding constrained section 94 can extend over less than all of the elastomeric strands 98.

As representatively shown, an advantageous configuration of the invention can have an arrangement in which each elastomeric member 34 includes a plurality of elastomeric strands 98 with a first set of at least one inboard strand, and a second set of at least one relatively outboard strand. Additionally, each restraint 84 can have a cross-directional extent which operates on at least one of the inboard strands, and operates on less than all of the inboard strands. In particular aspects each restraint 84 can be configured to have a cross-directional extent which operates on substantially all of the inboard strands. In another aspect, each restraint 84 can have a cross-directional extent which is configured to operate on less than all of the outboard strands, and to substantially avoid operating over at least one of the outboard strands. In desired configurations, at least the laterally outermost elastomeric strand is substantially free of the restraint 84.

Where each restraint 84 and its corresponding constrained section 94 are limited to extend over only a portion of the cross-wise extent of the elastomeric member (e.g. only a portion of the total number of elastomeric strands in the elastomeric member), the resulting side-by-side combination of constrained and unconstrained portions can better provide the desired pocket or bowl shape in the article when the article is worn. The unconstrained portions of the elastomeric member are able to stretch and expand to a relatively greater amount to further conform to the wearer's body, and can provide gradually increasing, increment amounts of greater stretchability to produce further gasketing immediately adjacent the constrained portions of the elastomeric member. The additional, incremental amounts of conformance of conformance and gasketing can provide better fit and better resistance to leakage.

The diaper 10 may include a waist elastic positioned in the longitudinal end margins of either or both of the front waistband 14 and the rear waistband 12. The waist elastics may be composed of any suitable elastomeric material, such as an elastomer film, an elastic foam, multiple elastic strands, an elastomeric fabric or the like. For example, suitable elastic waist constructions are described in U.S. Pat. No. 4,916,005 to Lippert et al., the entire disclosure of which is hereby incorporated by reference in a manner that is consistent herewith.

With reference to the representative configurations shown in FIGS. 1, 2 and 3, the article may include a system of "ear" regions or ear members 38. In particular arrangements, each ear region or member 38 extends laterally at the opposed, lateral ends of at least one waistband portion of backsheet 30, such as the representatively shown rear waistband portion 12, to provide terminal side sections of the article. In addition, each ear region can substantially span from a laterally extending, terminal waistband edge 76 to approximately the location of its associated and corresponding leg opening section of the diaper. The diaper 10, for example, has a laterally opposed pair of leg openings provided by the curved margins of the ear regions in combination with the correspondingly adjacent, medial sections of the shown pair of longitudinally extending, side edge regions 20 (e.g. FIG. 1). In alternative configurations, the ear regions may be provided by a system of separately provided ear members (not shown).

In the various configurations of the invention, the ear regions may be integrally formed with a selected diaper component. For example, ear regions 38 can be integrally formed from the layer of material which provides backsheet layer 30, or may be integrally formed from the material employed to provide topsheet 28. In alternative configurations, the ear regions 38 may be provided by one or more separately provided members that are connected and assembled to the backsheet 30, to the topsheet 28, in between the backsheet and topsheet, or in various fixedly attached combinations of such assemblies.

In particular configurations of the invention, each of the ear regions 38 may be formed from a separately provided piece of material which is then suitably assembled and attached to the selected front and/or rear waistband portion of the diaper article. For example, each ear region 38 may be attached to the rear waistband portion of the backsheet 30 along an ear region attachment zone, and can be operably attached to either or both of the backsheet and topsheet components of the article. The inboard, attachment zone region of each ear region can be overlapped and laminated with its corresponding, lateral end edge region of the waistband section of the article. The ear regions extend laterally to form a pair of opposed waist-flap sections of the diaper, and are attached with suitable connecting means, such as adhesive bonding, thermal bonding, ultrasonic bonding, clips, staples, sewing or the like. Desirably, the ear regions extend laterally beyond the terminal side edges of the backsheet layer and topsheet layer at the corresponding, attached waistband section of the article.

The ear regions 38 may be composed of a substantially non-elastomeric material, such as polymer films, woven fabrics, nonwoven fabrics or the like, as well as combinations thereof. In particular aspects of the invention, ear regions 38 may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 25. For example, suitable meltblown elastomeric fibrous webs for forming ear regions 38 are described in U.S. Pat. No. 4,663,220 issued May 5, 1987 to T. Wisneski et al., the entire disclosure of which is hereby incorporated by reference. Examples of composite fabrics comprising at least one layer of nonwoven textile fabric secured to a fibrous elastic layer are described in European Patent Application EP 0 217 032 A2 published on Apr. 8, 1987 which has the listed inventors of J. Taylor et al., the entire disclosure of which is hereby incorporated by reference. Examples of NBL materials are described in U.S. Pat. No. 5,226,992 issued Jul. 13, 1993 to Mormon, the entire disclosure of which is hereby incorporated by reference.

As previously mentioned, various suitable constructions can be employed to attach the ear regions 38 to the selected waistband portions of the article. Particular examples of suitable constructions for securing a pair of elastically stretchable members to the lateral, side portions of an article to extend laterally outward beyond the laterally opposed side regions of the outer cover and liner components of an article can be found in U.S. Pat. No. 4,938,753 issued Jul. 3, 1990 to P. VanGompel et al., the entire disclosure of which is hereby incorporated by reference in a manner that is consistent herewith.

Each of the ear regions 38 extends laterally at a one of the opposed lateral ends of at least one waistband section of the diaper 10. In the shown embodiment, for example, a first pair of ear regions extend laterally at the opposed lateral ends of the back waistband section of the backsheet 30, and a second pair of ear regions extend laterally at the opposed lateral ends of the front waistband section of the backsheet. The ear regions can have a tapered, curved or otherwise contoured shape in which the length of its inboard base region is smaller or larger than the length of its relatively outboard end region. The ear regions may, for example, have a substantially rectangular shape or a substantially trapezoidal shape.

Diaper 10 can also include a pair of elasticized containment flaps (not shown) which extend generally length-wise along the longitudinal direction 27 of the diaper. The containment flaps are typically positioned laterally inboard from the leg elastics 34, and substantially symmetrically placed on each side of the lengthwise, longitudinal centerline of the diaper. In the illustrated arrangements, each containment flap has a substantially fixed edge portion and a substantially moveable edge portion , and is operably elasticized with at least one elastomeric member to help each containment flap to closely contact and conform to the contours of the wearer's body. Examples of suitable containment flap constructions are described in U.S. Pat. No. 4,704,116 entitled DIAPERS WITH ELASTICIZED SIDE POCKETS issued Nov. 3, 1987, to K. Enloe, the entire disclosure of which is hereby incorporated by reference in a manner that is consistent herewith. The containment flaps may be composed of a wettable or a non-wettable material, as desired. In addition, the containment flap material may be substantially liquid-impermeable, may be permeable to only gas or may be permeable to both gas and liquid. Other suitable containment flap configurations are described in U.S. Pat. No. 5,562,650 entitled ABSORBENT ARTICLE HAVING AN IMPROVED SURGE MANAGEMENT by R. Everett et al., which issued Oct. 8, 1996, the disclosure of which is hereby incorporated by reference in a manner that is consistent herewith.

An extensible outercover 40 may be joined to extend over a major portion of the outward surface of the absorbent composite 32. The extensible outercover is desirably capable of providing a selected elongation when subjected to an applied tensile force. The extensible outercover is also desirably capable of providing a selected, sustained deformation, when subjected to an applied tensile force and then allowed to relax for a selected time period after removing the applied tensile force. The measurement of the selected time period begins immediately after the removal of the tensile force. Desirably, the sustained deformation is a substantially permanent deformation. The selected elongation and sustained deformation can occur at least along the lateral cross-direction 25 of the article. Optionally, the selected elongation and sustained deformation can occur along the longitudinal direction 27 of the article, or may occur along both the cross-direction and longitudinal direction of the article.

Examples of absorbent articles having an extensible outer cover are described in U.S. patent application Ser. No. 09/249434 entitled EXPANDABLE COVER GARMENT by P. T. VanGompel et al., which was filed Feb. 12, 1999. The entire disclosure of this document is incorporated herein by reference in a manner that is consistent herewith.

In particular aspects, the extensible outercover can provide an elongation of at least about 1 cm when subjected to a tensile force of 30 gmf per inch (per 2.54 cm). The extensible outercover can also provide a substantially permanent deformation of at least about 20%, when subjected to a tensile force of 50 gmf per inch (per 2.54 cm) and then allowed to relax, after a removal of the tensile force, for a period of 1 minute.

In further aspects of the invention, the extensible outercover 40 can be substantially non-elastomeric. Accordingly, the extensible outercover does not have the stretch and retraction characteristics of natural rubber. In other aspects, the absorbent article can include an expandable turned section 92 joined along at least a portion of each side region 20 of the absorbent composite 32 in the first end region 78 and/or second end region 79 of the absorbent composite. Each expandable, turned section 92 can be expandable at least along the cross-direction 25 or at least along an outward direction of said article, and each expandable attachment section is configured to secure its correspondingly joined side edge region of the absorbent composite to the outward surface 56 of its corresponding body panel 52 or 53.

The article of the invention incorporates a distinctive, separately provided extensible outercover 40 which includes an extensible fabric layer which is operatively attached or otherwise joined to extend over a major portion of the outward surface of the article. In particular, the extensible outercover 40 can extend over a major portion of the outward surface of the absorbent composite 32. Desirably, the extensible outercover can extend over substantially an entire area of the outward surface of the absorbent composite. The selected extensibility in the outercover can allow the outercover to accommodate and cooperate with the properties of the other materials or components to which the extensible outercover is attached in the article. In regions where the outercover is not affixed to the article, the extensible outercover can be free to advantageously expand with minimal force and with a high amount of permanent deformation.

Extensible regions in the outercover 40 are provided in areas where the outercover is not directly affixed to the article. In the article of the invention, the extensible regions can desirably be located over the regions of the absorbent composite which are appointed for expansion during the absorption of liquids. For example, the absorbent composite can expand outwardly during use, and the outercover can elongate and extend in correspondence with the expansion of the absorbent composite and/or other components of the article. In desired aspects, the outercover 40 can be extensible along the transverse lateral direction 25. In optional aspects, the outercover can be extensible along the longitudinal direction 27, or along a combination of both the lateral and longitudinal directions.

Elasticized regions in the outercover 40 can be created where the extensible outercover is affixed to an elastomeric component. For example, an elastomeric region in the outercover 40 can be created where the extensible outercover is affixed to an elastomerically stretchable body panel 52. Substantially non-extensible regions in the outercover can be created where the extensible outercover 40 is affixed to a substantially non-extensible component. For example, a substantially non-extensible region in the outercover 40 can be created where the extensible outercover 40 is affixed to a substantially non-extensible component, such as a substantially non-extensible substrate layer (e.g. the topsheet 28 or backsheet 30) of the article.

Figure 1A:
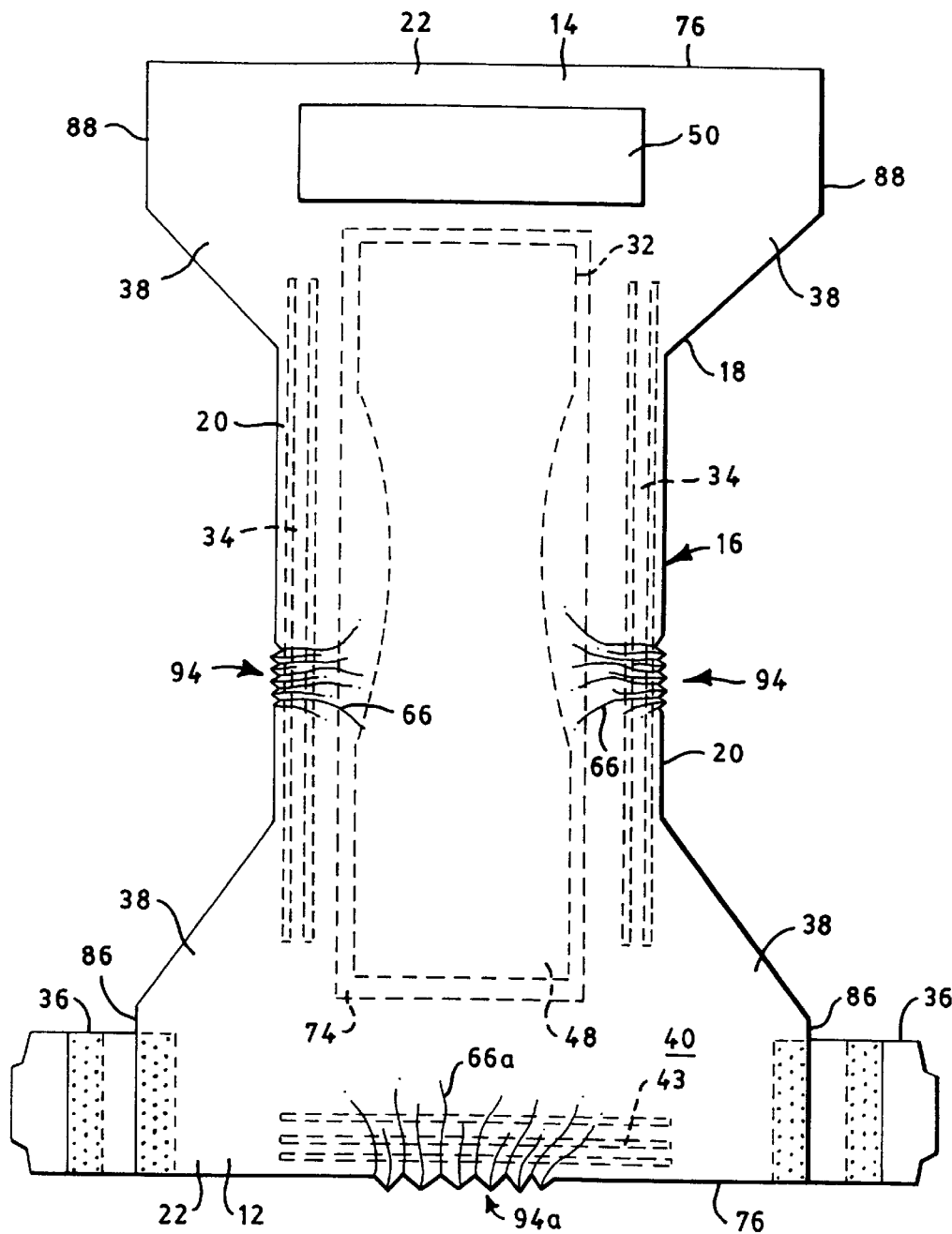
FIG. 1A representatively shows a top plan view of the outward side surface of an article of the invention.

In particular configurations, the substantially non-extensible regions of the outercover member 40 can be constructed by affixing the extensible nonwoven fabric of the outercover to a substantially non-extensible component, such as a substantially non-extensible backsheet layer 30. With reference to FIG. 1A, for example, the resultant non-extensible region can provide a landing zone region 50 which is composed of an integral portion of the nonwoven fabric of the extensible outercover. The backsheet layer 30 of the absorbent composite 32 can, for example, be composed of a substantially non-extensible polymer film, and the nonwoven fabric of the extensible outercover 40 can be adhesively attached or otherwise affixed to the front waistband region of the backsheet layer with a selected outercover attachment, which may be substantially non-extendible. The outercover attachment may be irregularly or randomly distributed, or may be arranged in a predetermined, pattern array, such as the representatively shown swirl pattern. The nonwoven fabric can thereby provide a complementary component of an interengaging mechanical fastening system. For example, the affixed portion of the outercover in the landing zone 50 can provide a female loop component of a mechanical hook-and-loop fastening system. The affixing of the extensible outercover material to the polymer film can prevent the necked fabric from excessively elongating and extending in the lateral direction during the ordinary operation of the fastening system.

As representatively shown, the front waistband section 14 of the diaper 10 has a laterally opposed, front pair of side edge regions 88, and the rear waistband section 12 has a laterally opposed, rear pair of side edge regions 86. The intermediate section 16 interconnects the front and rear waistband section and provides a diaper crotch region which is typically positioned between the legs of the wearer. The article has an appointed fastener landing member 50 which is disposed on the outward surface of the article. In the example representatively shown in FIG. 3, for example, the landing member 50 can be disposed on the outward surface of the backsheet layer 30. The liquid permeable topsheet layer 28 is superposed in facing relation with the backsheet layer 30, and the retention portion 48 is operably connected and affixed between the backsheet layer 30 and topsheet layer 28. In desired arrangements, the topsheet layer 28 and the retention portion 48 can be constructed to be substantially nonelastomeric and can be operatively attached to the backsheet member 30 to substantially restrain excessive stretching of the backsheet member.

To provide a desired refastenable fastening system, the diaper 10 can include one or more appointed landing zone regions, such as a first, primary landing zone 50 (e.g. FIGS. 1A, 1C and 1E), which can provide an operable target area for receiving a releasable and re-attachable securement of the fastener tabs 36 thereon. In particular embodiments of the invention, the landing zone patch can be positioned on the front waistband portion 14 of the diaper and is located on the outward surface of the backsheet layer 30. Alternatively, the landing zone patch can be positioned at the rear waistband portion 12 of the article, or optionally may be disposed on an appointed inward surface of the article, such as the bodyside surface of the topsheet layer 28. The fastening mechanism between the landing zone and the fastener tabs 36 may be adhesive, cohesive, mechanical or combinations thereof. In the context of the present invention, a mechanical fastening system is a system which includes cooperating components which mechanically inter-engage to provide a desired securement.

The mechanical fastener components can be provided by mechanical-type fasteners such as hooks, buckles, snaps, buttons and the like, which include cooperating and complementary, mechanically interlocking components. For example, the mechanical fastening system may be a hook-and-loop type of fastening system. Such fastening systems generally comprise a "hook" or hook-like, male component, and a cooperating "loop" or loop-like, female component which engages and releasably interconnects with the hook component. Desirably, the interconnection is selectively releasable and re-attachable over several cycles. Conventional systems are, for example, available under the VELCRO trademark. The elements of the hook component may be provided by a single or multiple hook configuration, such as provided by a mushroom-head type of hook element. The elements of the loop component may be provided by a woven fabric, a nonwoven fabric, a knitted fabric, a perforated or apertured layer, and the like, as well as combinations thereof. The many arrangements and variations of such fastener systems have been collectively referred to as hook-and-loop fasteners.

A configuration which employs a releasable, interengaging mechanical fastening system can, for example, locate the first component of the mechanical fastener, such as a hook material 70 (e.g. FIG. 1 D), on the fastener tab 36; and can locate a second, cooperating component of the mechanical fastener, such as a loop material 72 (e.g. FIG. 1C ), on the landing zone 50. It should also be readily apparent that, in the various configurations of the invention, the relative positions and/or materials of the fastening component and its corresponding landing zone component can be transposed. Accordingly, the first component of the mechanical fastener can be located on the landing zone 50 and the second, cooperating component of the mechanical fastener can be located on the fastener tab 36.

Examples of suitable hook-and-loop fastening systems are described in U.S. Pat. No. 5,019,073 issued May 28, 1991 to T. Roessler et al., the entire disclosure of which is hereby incorporated by reference in a manner that is consistent herewith. Other examples of hook-and-loop fastening systems are described in U.S. patent application Ser. No. 366,080 entitled HIGH-PEEL TAB FASTENER, filed Dec. 28, 1994 by G. Zehner et al. which issued as U.S. Pat. No. 5,605,735; and U.S. patent application Ser. No. 421,640 entitled MULTI-ATTACHMENT FASTENING SYSTEM, filed Apr. 13, 1995 by P. VanGompel et al.; the entire disclosures of which are hereby incorporated by reference in a manner that is consistent herewith. Examples of fastening tabs constructed with a carrier layer are described in U.S. Pat. No. 08/603,477 of A. Long et al., entitled MECHANICAL FASTENING SYSTEM WITH GRIP TAB and filed Mar. 6, 1996, now U.S. Pat. No. 5,624,429 issued Apr. 29, 1997, the entire disclosure of which is hereby incorporated by reference in a manner which is consistent herewith.

In the various embodiments of the invention, a separately provided tape fastener tab 36 can be located at either or both of lateral end regions 86 and 88 of either or both of the waistbands 14 and 12, respectively. The representatively shown embodiment, for example, has at least one of the fastener tabs 36 located at each of the distal side edges of the rear waistband 12. More particularly, each of the fasteners 36 is assembled and attached to extend from a corresponding, immediately adjacent ear region provided at one of the laterally opposed, distal ends of the first body panel 52.

In the representatively shown hook-and-loop fastening system, the hook material is operably connected to the fastening tab 36, and the loop material is employed to construct at least one cooperating landing zone 50. The landing zone may, for example, be disposed on the outward surface of the backsheet 30. As representatively shown, the landing zone can be suitably positioned on the exposed, outward-side surface of the second, front body panel 53. An alternative configuration of the hook-and-loop fastening system may have the loop material secured to the fastener tab 36 and the hook material employed to form the landing zone 50. Each appointed landing zone may be a separately provided member assembled to the appropriate body panel 52 or 53, or may be integrally formed with the body panel. For example, the outward surface of the body panel 53 may be composed of a fabric that provides an operative loop material for the fastening system.

In the various aspects and configurations of the invention, the hook element material can be of the type referred to as micro-hook material. A suitable micro-hook material is distributed under the designation CS200 and is available from 3M Company, a business having offices in St. Paul, Minn. The micro-hook material can have hooks in the shape of mushroom "caps", and can be configured with a hook density of about 1600 hooks per square inch; a hook height which is within the range of about 0.033–0.097 cm (about 0.013 to 0.038 inch); and a cap width which is within the range of about 0.025–0.033 cm (about 0.01 to 0.013 inch). The hooks are attached to a base film substrate having a thickness of about 0.0076–0.01 cm (about 0.003–0.004 inch) and a Gurley stiffness of about 15 mgf. Another suitable micro-hook material is distributed under the designation VELCRO CFM-29 1058, and is available from VELCRO U.S.A., Inc., a business having offices in Manchester, New Hampshire. The micro-hook material can have hooks in the shape of angled hook elements, and can be configured with a hook density of about 264 hooks per square centimeter (about 1700 hooks per square inch); a hook height which is within the range of about 0.030–0.063 cm (about 0.012–0.025 inch); and a hook width which is within the range of about 0.007 to 0.022 cm (about 0.003 to 0.009 inch). The hook elements are coextruded with a base layer substrate having a thickness of about 0.0076–0.008 cm (about 0.003–0.0035 inch), and the member of hook material has a Gurley stiffness of about 12 mgf (about 12 Gurley units).

For the purposes of the present invention, the various stiffness values are determined with respect to a bending moment produced by a force which is directed perpendicular to the plane substantially defined by the length and width of the component being tested. A suitable technique for determining the stiffness values described herein is a Gurley Stiffness test, a description of which is set forth in TAPPI Standard Test T 543 om-94 (Bending Resistance of Paper (Gurley type tester)). A suitable testing apparatus is a Gurley Digital Stiffness Tester; Model 4171-D manufactured by Teledyne Gurley, a business having offices in Troy, N.Y. For purposes of the present description, the stated Gurley stiffness values are intended to correspond to the values that would be generated by a "standard" sized sample. Accordingly, the scale readings from the Gurley stiffness tester are appropriately converted to the stiffness of a standard size sample, and are traditionally reported in terms of milligrams of force (mgf). Currently, a standard "Gurley unit" is equal to a stiffness value of 1 mgf, and may equivalently be employed to report the Gurley stiffness.

In the various aspects and configurations of the invention, the loop material can be provided by a nonwoven, woven or knit fabric. For example, a suitable loop material fabric can be composed of a 2 bar, warp knit fabric of the type available from Guilford Mills, Inc., Greensboro, N.C. under the trade designation #34285, as well other of knit fabrics. Suitable loop materials are also available from the 3M Company, which has distributed a nylon woven loop under their SCOTCHMATE brand. The 3M Company has also distributed a liner-less loop web with adhesive on the backside of the web, and 3M knitted loop tape.

In particular aspects of the invention, the loop material need not be limited to a discrete landing zone patch. Instead the loop material can, for example, be provided by a substantially continuous, outer fibrous layer which is integrated to extend over substantially the total exposed surface area of a cloth-like outer cover employed with the diaper 10. The resultant, cloth-like backsheet 30 can thereby provide the loop material for an operative "fasten anywhere" mechanical fastening system.

In the various configurations of the invention, the engagement force between the particular fastening component and its appointed landing zone component should be large enough and durable enough to provide an adequate securement of the article on the wearer during use.

Each of the fastening components and elements in the various constructions of the invention may be operably attached to its supporting substrate by employing any one or more of the attachment mechanisms employed to construct and hold together the various other components of the article of the invention. The fastening elements in the various fastening regions, may be integrally formed, such as by molding, co-extrusion or the like, along with the associated substrate layer. The substrate layer and its associated mechanical fastening elements may be formed from substantially the same polymer material, and there need not be a discrete step of attaching the fastening elements to an initially separate substrate layer. For example, the individual hook elements may be integrally formed simultaneously with a hook base-layer by coextruding the base layer and hook elements from substantially the same polymer material.

It should be readily appreciated that the strength of the attachment or other interconnection between the substrate layer and the attached fastening component should be greater than the peak force required to remove the fastener tab 36 from its releasable securement to the appointed landing zone of the article.

EXAMPLES

The following examples are presented to provide a more detailed understanding of the invention. The example is representative, and are not intended to limit the scope of the invention.

Example 1

A representative example of the invention provided a size-3 or medium-size diaper for an infant weighting between 16 to 28 pounds. The diaper generally had the configurations and shapes illustrated in FIGS. 3 through 3F. The front ("second") body panel 53 measured 11 inches along the cross-direction and 4.5 inches along the longitudinal direction, and was composed of a 1.0 osy (34 g/m$^2$) polypropylene spunbond fabric. The back ("first") body panel 52 measured 11 inches along the cross-direction and 5.75 inches along the longitudinal direction, and was made of a necked-bonded-laminate material which had a basis weight of 77 g/m$^2$ and was laterally stretchable 20–40% in the cross-direction. The desired curvatures were formed along the medial portions of the inboard edges 64 and 65 of the back and back panels 52 and 53, respectively. Four, 0.25 inch wide strips of 3M-927 two-sided adhesive tape were applied to attach the expandable attachment sections 92 of the absorbent composite to the front and back panels at the four side securement sections 42.

The absorbent body composite 32 included a substantially liquid-impervious backsheet layer 30 which measured 8 inches along the cross-direction and 14 inches in the longitudinal direction, and was composed of a 0.75 mil thickness, polyethylene film. A cellulose tissue wrap sheet 74 was overlaid onto and wrapped around a retention portion 48 that was composed of a mixture of 63% cellulosic, woodpulp fluff and 37% superabsorbent polymer (FAVOR 880 from Stockhausen). The wrapped retention portion was debulked to a thickness of 0.2 inch, and cut to an hourglass shape. The shaped retention portion measured 12 inches in the longitudinal direction, and had a narrowed crotch which measured 3.5 inches in the cross-direction. The two, longitudinally opposed ends of the retention portion measured about 4 inches in the cross-direction. A layer of surge material 46 was adhesively attached to the front of the tissue wrap at a location spaced about 2 inches from the front-most edge of the tissue wrap. The surge layer had a basis weight of 2.5 osy and a density of 0.024 g/cm$^3$, and measured 3 inches in the cross-direction and 6 inches in the longitudinal direction. A light spray of adhesive was applied to the backsheet layer to attach the backsheet layer to the tissue wrapped retention portion. The front-most edge of the tissue wrap sheet was placed about 0.75 inch inboard from the leading, front-most edge of the backsheet layer, and a light spray of adhesive attached the top, bodyside surface of the surge layer 46 to the outward surface of the liquid-permeable topsheet layer 28. The topsheet was composed of a 0.5 osy polypropylene spunbond fabric treated with 0.3% surfactant, and was placed over the surge layer 46, the wrapsheet 74 and the retention portion 48. The topsheet was adhesively bonded to the various absorbent components and to the perimeter of backsheet layer to create the assembled, absorbent body composite.

To form the expandable attachment sections 92, the side edge regions 20 of the topsheet and backsheet layers in the absorbent body composite 32 were folded and tucked to create z-folded pleats. The inward facing, topsheet portion of the z-folded pleat was then attached to the outward-facing surfaces of the front and back panels with the 0.25 inches (6.35 mm) wide strips of adhesive located at the four side securement sections 42. Accordingly the absorbent body composite 32 was assembled and joined to interconnect and bridge between the spaced-apart front body panel 53 and back body panel 52.

A very narrow width of spray adhesive was selectively applied down the center of the backsheet layer 30 of the absorbent composite 32. The spray adhesive was also applied to the exposed, outward, non-bodyside of the front and back body panels 52 and 53. Care was taken to not spray the adhesive into the z-folded pleats of the absorbent composite. Additionally, a narrow width of adhesive was sprayed across each of the two longitudinally opposed ends of the absorbent composite, to seat the absorbent ends. A single piece of 60% necked, polypropylene spunbond fabric at a basis weight of 1.2 g/m$^2$ was placed over the outward side of the absorbent composite and the outward side of the exposed body panels to provide the extensible outercover layer 40. The necked spunbond fabric was attached at the sprayed adhesive zones, and a rotary cutter was employed to cut out the excess material to the shape of the garment. Each leg elastic member 34 included two, 940 dtx elastomeric strands 98 composed of LYCRA XA SPANDEX. The elastomeric strands were elongated to a 300% elongation, and adhesively laminated to a 0.4 osy polypropylene spunbond facing member 96 with a Findley adhesive H2525A. The assembled, composite leg elastic member was stretched-to-stop, and ultra-sonically point-bonded to the side marginal edges of the backsheet layer 30. In particular, each elastic member was located on the outward facing surface of the backsheet layer and positioned adjacent to and laterally outboard from a fold-region of its corresponding, expandable attachment section 92. Additionally, the stretched elastic members 34 were interposed and sandwiched between the backsheet layer 30 and the extensible outercover layer 40, and were adhesively attached therebetween to provide elastomerically contracted gathers 66 in each of the side edge margins 20. Longitudinal end portions of each leg elastic member 34 were attached to portions of the absorbent composite that were overlaid by the front and back body panels. As a result, each of the laterally opposed pair of leg elastic members 34 created a gathered region at its corresponding leg opening of the diaper.

A restraint composed of a 25 mm×25 mm ultrasonic bond was applied to the central region of each set of contracted gathers 66 to create a corresponding constrained section 94, and the restraint operatively restricted a re-expansion of its corresponding constrained section of the gathers, and effectively prevented a complete re-expansion of the gathers. As a result, the stretch-to-stop longitudinal length 96 of each side edge margin 20 was relatively shorter than the stretch-to-stop, longitudinal length 26 of the other, unrestrained portions of the garment. When the article side margins were tensioned and stretched-to-stop, the restrained and shortened side edge margins created a configuration in which there was an incomplete flattening of the more central, medial portion of the article that are located laterally-between the leg elastic members. As a result, the medial portion was substantially prevented from being extended to its flat-out condition, and the loosely arranged medial portion of the article was able to form a pocket region having a discrete void volume.

Mechanical, hook-type fastener tabs 36 were adhesively and ultrasonically bonded to the ear portions 38 of the back body panel 52 of the diaper article. In a preferred arrangement, the longitudinally terminal edges of the fastener tabs were substantially aligned with the end edge 60 of the back body panel 52 at the waistband side edge regions 86.

Example 2

A suitable technique for generating a representative tensile-load vs. extension curve to determine the effect of a restraint on the tensile behavior of a constrained section can employ ASTM Standard Test Method D882 (Tensile Method for Tensile Properties of Thin Plastic Sheeting) dated December 1995, with the following particulars. The "width" of a test sample will be a cross-wise width which can be conveniently obtained from the product being tested, and is desirably about 0.5 inch (13 mm). The test sample width is perpendicular to the direction of the tensile force applied during the testing. The initial separation between jaws of a tensile tester is 2 inches (51 mm). The moving jaw is moved at a constant speed of 50 mm/min away from the stationary jaw and stops at an extension about 100 mm. The tensile test is carried out on a standard tensile tester, such as a SINTECH tester. The load-extension curve can be recorded on a conventional computer equipped with commercially available software, such as TestWorks for Windows, Version 3.10. Both the SINTECH tester and the TestWorks software are available from MTS Corporation, a business having a location at 1400 Technology Drive, Eden Prairie, Minn.

The elastomeric composite for this example was composed of two layers of 0.4 osy (14 g/m$^2$) nonwoven polypropylene spunbond with three strands (spaced 4 mm apart) of 740 decitex LYCRA elastomer elongated to 235% and adhesively sandwiched between the two nonwoven layers. A FINDLEY adhesive H-2525A was sprayed (at an add-on of 5–8 grams per square meter) over the elongated LYCRA strands and nonwoven layers, and the strands were sandwiched between the two nonwoven layers. The composite was slit to a width of 13 mm (the LYCRA strands in the composite were positioned 4 mm apart and 2 mm from each edge) and allowed to elastomerically contract. The composite was allowed to retract, and the retracted composite was cut to sample lengths of 7.0 inch (178 mm). The control sample A was non-bonded. The constrained test sample B included a restraint composed of ultrasonic bonds. More particularly, sample B was ultrasonically bonded by employing a 0.75 inch (19 mm) flat anvil to create a 0.5 inch (13 mm) bond along substantially the full length of the contracted, composite sample.

The two nonwoven fabrics were composed of PC-973 polypropylene obtained from Montell, USA, Inc., a business having offices in Wilmington, Del., 19850. The spunbond fibers were formed at the 0.4 osy (13.6 g/m$^2$) basis weight and thermally bonded with a wire-weave bond pattern at a 12% to 17% bond area. The 740 decitex LYCRA elastomer is available from E.I. DuPont de Nemours and Company, a business having offices in Wilmington, Dele. The FINDLEY H-2525A adhesive is available from Findley Adhesives, a business having offices in Milwaukee, Wisconsin. The composite was constructed on a laminator (Model # TC-380) made by J & M Labs, a business having offices located in Dawsonville, Ga. The test code retracted samples were bonded with a 0.75" (19 mm) anvil using a DUKANE ULTRA 2000 bonder with a weld time setting of 0.170 sec and a hold time of 0.140 sec. This bonder is available from Dukane Ultrasonics, a business having offices at 2900 Dukane Drive, St. Charles, Ill. 60174.

Figure 4:
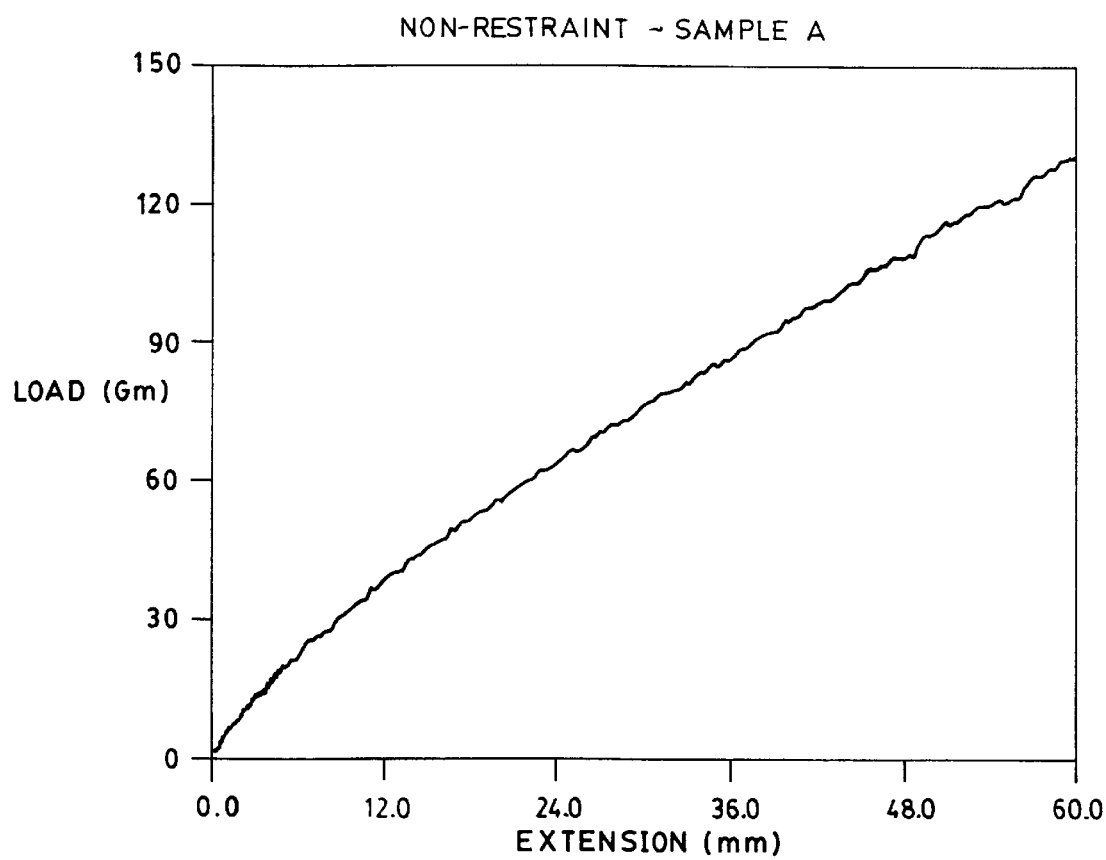
FIG. 4 is a graph which representatively shows the stress-strain properties of an elastomeric, composite sample that does not include a restraint component.
Figure 5:
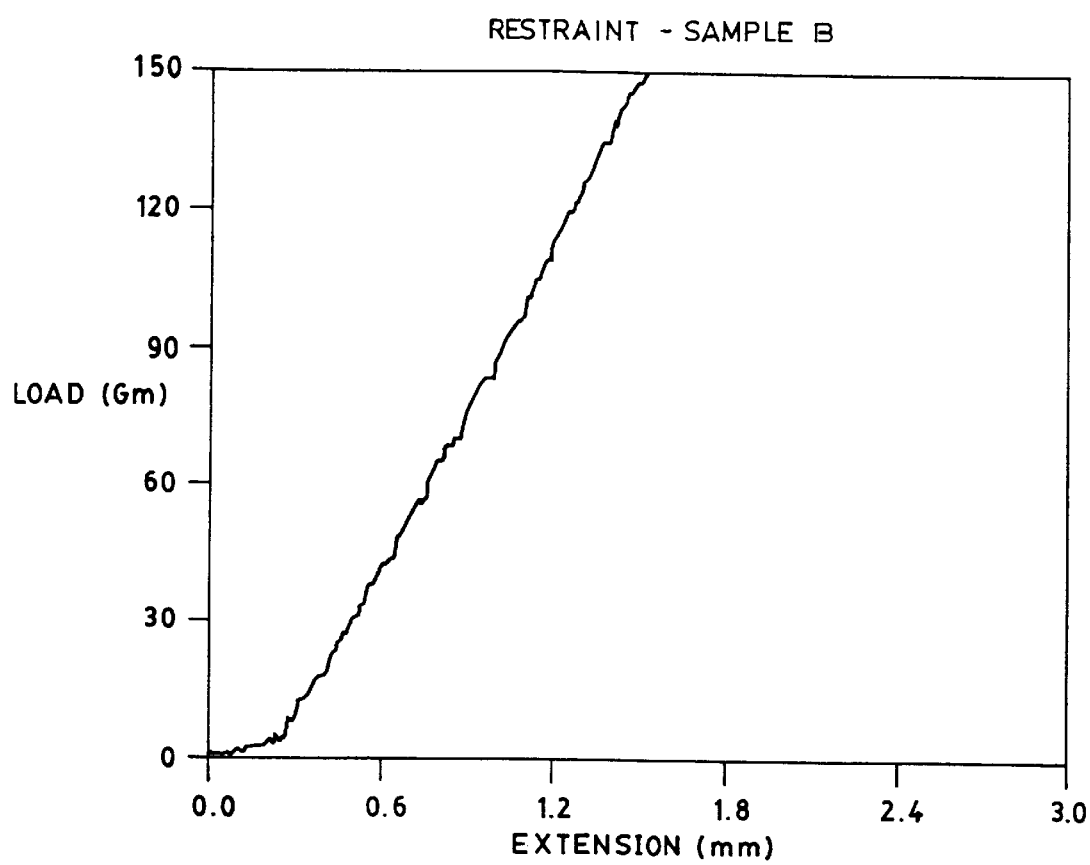
FIG. 5 is a graph which representatively shows the stress-strain properties of an elastomeric, composite sample that includes an operative restraint component.

The two samples described above were tested to determine their tensile-load vs. extension curves. Sample A did not include a restraint; Sample B included a restraint. Test results are shown in FIGS. 4 and 5. For sample A, the extension was about 44 mm under a tensile load of 100 grams, as shown in FIG. 4. For sample B, the extension was only about 1.1 mm under 100 grams of tensile load, as shown in FIG. 5. This demonstrates how the presence of the restraint can restrict the extensibility of an elastic member.

Since each sample had a cross-wise width of 0.5 inch (13 mm) and a length of 2 inches (51 mm) between jaws, the results also indicate that, under a tensile force of 200 gram per inch (about 0.77 Newton per centimeter), sample A exhibited an 86% elongation, while sample B exhibited only a 2.2% elongation. It should be noted that the amount of the %-elongation under a given tensile load can be tailored by changing the dimension of a restraint in either its lengthwise or cross-wise direction.

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. A integral absorbent article having a longitudinal length direction, a lateral width direction, and at least one edge margin, said article comprising:
    a substantially liquid-impermeable backsheet layer, a liquid permeable topsheet layer, and a retention portion sandwiched between said backsheet and topsheet layers; wherein
    said edge margin includes an elastomeric member joined to provide elastomerically contracted gathers in said edge margin;
    said edge margin includes a restraint applied to an appointed portion of said gathers in said edge margin to operatively restrict a re-expansion of a constrained section of said gathers in said edge margin; and
    said constrained section has lengthwise extent which is at least about 10 mm.

2. An integral absorbent article as recited in claim 1, wherein said at least one edge margin is a longitudinal end margin.

3. An integral absorbent article as recited in claim 1, wherein said at least one edge margin is a lateral side margin.

4. An article as recited in claim 1, wherein said restraint includes an area of inter-attachment between individual gathers.

5. An article as recited in claim 4, wherein said restraint includes an adhesive.

6. An article as recited in claim 4, wherein said restraint includes a separately provided mechanical attachment.

7. An article as recited in claim 4, wherein said restraint includes a system of thermal bonds.

8. An article as recited in claim 4, wherein said restraint includes a system of sonic bonds.

9. An article as recited in claim 1, wherein said constrained section exhibits a lengthwise extension of not more than about 6 mm when subjected to a tensile force of 0.77 N/cm.

10. An article as recited in claim 1, wherein said constrained section exhibits a lengthwise extension of not more than about 8% when subjected to a tensile force of 0.77 N/cm.

11. An article as recited in claim 1, wherein said constrained section has lengthwise extent which is up to about 70 mm.

12. An article as recited in claim 1, wherein said elastomeric member includes a plurality of elastomeric strands; and said restraint is configured to operate on substantially all of said strands.

13. An integral absorbent article having a longitudinal length direction, a lateral width direction, and at least one edge margin, said article comprising:
    a substantially liquid-impermeable backsheet layer, a liquid permeable topsheet layer, and a retention portion sandwiched between said backsheet and topsheet layers; wherein
        said edge margin includes an elastomeric member joined to provide elastomerically contracted gathers in said edge margin;
    said edge margin includes a restraint applied to an appointed portion of said gathers in said edge margin to operatively restrict a re-expansion of a constrained section of said gathers in said edge margin; and
    said constrained section of said gathers in said edge margin includes a separately provided holder member attached to a limited portion of said gathers to provide said restraint in said constrained section.

14. An article as recited in claim 13, wherein said separately provided, holder member is substantially nonelastomeric.

15. An article as recited in claim 13, wherein said separately provided, holder member is substantially non-extensible.

16. An integral absorbent article having a longitudinal length direction, a lateral width direction, and at least one edge margin, said article comprising:
    a substantially liquid-impermeable backsheet layer, a liquid permeable topsheet layer, and a retention portion sandwiched between said backsheet and topsheet layers; wherein
    said edge margin includes an elastomeric member joined to provide elastomerically contracted gathers in said edge margin;
    said edge margin includes a restraint applied to an appointed portion of said gathers in said edge margin to operatively restrict a re-expansion of a constrained section of said gathers in said edge margin; and
    said constrained section has crosswise extent which is at least about 0.3 mm.

17. An article as recited in claim 16, wherein said constrained section has crosswise extent which is not more than about 25 mm.

18. An integral absorbent article having a longitudinal length direction, a lateral width direction, and at least one edge margin, said article comprising:
    a substantially liquid-impermeable backsheet layer, a liquid permeable topsheet layer, and a retention portion sandwiched between said backsheet and topsheet layers; wherein
    said edge margin includes an elastomeric member joined to provide elastomerically contracted gathers in said edge margin;
    said edge margin includes a restraint applied to an appointed portion of said gathers in said edge margin to operatively restrict a re-expansion of a constrained section of said gathers in said edge margin; and
    said restraint provides a reduced, extended length of said edge margin which is not more about 98% of an original, extended length of said edge margin.

19. An integral absorbent article having a longitudinal length direction, a lateral width direction, and at least one edge margin, said article comprising:
    a substantially liquid-impermeable backsheet layer, a liquid permeable topsheet layer, and a retention portion sandwiched between said backsheet and topsheet layers; wherein
    said edge margin includes an elastomeric member joined to provide elastomerically contracted gathers in said edge margin;
    said edge margin includes a restraint applied to an appointed portion of said gathers in said edge margin to operatively restrict a re-expansion of a constrained section of said gathers in said edge margin; and
    said restraint provides a reduced, extended length of said edge margin which is not less than about 85% of an original, extended length of said edge margin.

20. An integral absorbent article having a longitudinal length direction, a lateral width direction, and at least one edge margin, said article comprising:

a substantially liquid-impermeable backsheet layer, a liquid permeable topsheet layer, and a retention portion sandwiched between said backsheet and topsheet layers; wherein said edge margin includes an elastomeric member joined to provide elastomerically contracted gathers in said edge margin;

said edge margin includes a restraint applied to an appointed portion of said gathers in said edge margin to operatively restrict a re-expansion of a constrained section of said gathers in said edge margin;

said elastomeric member includes a plurality of elastomeric strands; and said restraint is configured to operate on less than all of said strands.

21. An article as recited in claim 20, wherein said elastomeric member includes a plurality of elastomeric strands with a first set of at least one inboard strand and a second set of at least one relatively outboard strand; and said restraint has cross-directional extent which substantially avoids operating over at least one of said outboard strands.

22. An article as recited in claim 20, wherein said elastomeric member includes a plurality of elastomeric strands with a first set of at least one inboard strand and a second set of at least one relatively outboard strand; and said restraint has cross-directional extent which operates on at least one of said inboard strands.

23. An article as recited in claim 20, wherein said elastomeric member includes a plurality of elastomeric strands with a first set of a first plurality of inboard strand and a second set of a second plurality of outboard strands; and said restraint has cross-directional extent.

24. An integral absorbent article having a longitudinal length direction, a lateral width direction, a pair of laterally opposed side margins and a pair of longitudinally opposed end margins;, said article comprising:

a substantially liquid-impermeable backsheet layer, a liquid permeable topsheet layer, and a retention portion sandwiched between said backsheet and topsheet layers; wherein each side margin includes an elastomeric member joined to provide elastomerically contracted gathers in said each side margin;

each side margin includes a side margin restraint applied to an appointed portion of said gathers in said each side margin to operatively restrict a re-expansion of a constrained section of said gathers in said each side margin;

at least one of said end margins includes a waist elastomeric member joined to provide elastomerically contracted waist gathers in said end margin; and said at least one end margin includes an end margin restraint applied to an appointed portion of said waist gathers in said at least one end margin to operatively restrict a re-expansion of a constrained section of said waist gathers in said at least one end margin.

25. An article as recited in claim 24, wherein said constrained section of said gathers in said each side margin is located approximately adjacent a juncture between an intermediate portion of said each side margin, and a laterally outward extending ear portion of said article.

26. An article as recited in claim 24, wherein said side margin restraint is applied to an intermediate, crotch portion of said each side margin to operatively restrict a re-expansion of a constrained section of said gathers located in the intermediate portion of said each side margin.

27. An article as recited in claim 26, wherein each said constrained section of said gathers is offset towards a back waistband in of said article.

28. An integral absorbent article having a longitudinal article length direction and a lateral article width direction, said article comprising:

an absorbent composite having first and second longitudinally opposed end regios, a pair of laterally opposed side margins, a bodyside surface, an outward surface, and a first longitudinally terminal end edge, said absorbent composite including a substantially liquid-impermeable backsheet layer, a liquid permeable topsheet layer, and a retention portion sandwiched between said backsheet and topsheet layers; each side margin of said absorbent composite including an elastomeric member joined to provide elastomerically contracted gathers in said each side margin; and each side margin of said absorbent composite including a restraint applied to an appointed portion of the gathers in said each side margin to operatively restrict a re-expansion of a constrained section of the gathers in said each side margin.

29. An article as recited in claim 1, further comprising an extensible outercover joined to extend over a major portion of said outward surface of said absorbent composite, said extensible outercover capable of providing a sustained deformation when subjected to a tensile stress and then allowed to relax under a zero applied stress.

30. An article as recited in claim 28, further comprising a first body panel joined to said first longitudinal end region of said absorbent composite, said first body panel having a first panel length which is less an said article length.

31. An article as recited in claim 30, wherein said absorbent composite is joined on an outward side surface of said first body-panel.

32. An article as recited in claim 31, wherein said absorbent composite is joined on an outward side surface of said first body panel with at least one expandable attachment section.

33. An article as recited in claim 28, further comprising a second body panel joined to said second longitudinal end region of said, absorbent composite, said second body panel having a second panel length which is less than said article length.

34. An article as recited in claim 33, wherein said absorbent composite is joined on an outward side surface of said second body panel.

35. An article as recited in claim 34, wherein said absorbent composite is joined on an outward side surface of said second body panel with at least one expandable attachment section.

* * * * *

UNITED STATES PATENT AND TRADEMARK OFFICE
CERTIFICATE OF CORRECTION

PATENT NO. : 6,361,527 B1
DATED : March 26, 2002
INVENTOR(S) : Paul Theodore Van Gompel and Yung Hsiang Huang It is certified that error appears in the above-identified patent and that said Letters Patent is hereby corrected as shown below:

Column 35,
Line 34, insert -- which operates on less than all of said inboard strands. -- after "extent".

Column 36,
Line 16, delete "regios" and substitute -- regions --.
Line 30, delete "margin." and insert -- margin, wherein said constrained section has a lengthwise extent which is at least 10 mm, and a crosswise extent which is at least about 0.3 mm; and said restraint provides a reduced extended length of said each side margin which is not more than about 98% of an original, extended length of said side margin --
Line 31, delete "1" and substitute -- 28 --.

Signed and Sealed this

Ninth Day of December, 2003

JAMES E. ROGAN
*Director of the United States Patent and Trademark Office*